US010001052B2

United States Patent
Imaeda

(10) Patent No.: US 10,001,052 B2
(45) Date of Patent: Jun. 19, 2018

(54) COMBUSTION STATE ESTIMATION METHOD

(71) Applicant: TOYOTA JIDOSHA KABUSHIKI KAISHA, Toyota-shi (JP)

(72) Inventor: Munenori Imaeda, Nagoya (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 339 days.

(21) Appl. No.: 15/052,242

(22) Filed: Feb. 24, 2016

(65) Prior Publication Data
US 2016/0252003 A1  Sep. 1, 2016

(30) Foreign Application Priority Data

Feb. 26, 2015 (JP) ................ 2015-037160

(51) Int. Cl.
| | |
|---|---|
| G06F 19/00 | (2018.01) |
| F02B 5/02 | (2006.01) |
| F02D 35/02 | (2006.01) |
| G01N 25/22 | (2006.01) |
| F02D 41/00 | (2006.01) |
| F02D 41/14 | (2006.01) |

(52) U.S. Cl.
CPC .............. *F02B 5/02* (2013.01); *F02D 35/028* (2013.01); *G01N 25/22* (2013.01); *F02D 2041/001* (2013.01); *F02D 2041/1412* (2013.01); *F02D 2041/1433* (2013.01)

(58) Field of Classification Search
CPC ......... F02B 5/02; G01N 25/22; F02D 35/028; F02D 2041/1433; F02D 2041/1412; F02D 2041/001
See application file for complete search history.

(56) References Cited

U.S. PATENT DOCUMENTS

| | | | | |
|---|---|---|---|---|
| 6,276,334 B1* | 8/2001 | Flynn | ................ | F02B 19/14 |
| | | | | 123/435 |
| 2005/0229903 A1* | 10/2005 | Kobayashi | ............ | F02D 35/023 |
| | | | | 123/435 |
| 2015/0369165 A1* | 12/2015 | Nagano | ................... | F02D 41/40 |
| | | | | 701/104 |

FOREIGN PATENT DOCUMENTS

| | | |
|---|---|---|
| JP | 2007-177654 | 7/2007 |
| WO | WO 2015/162970 A1 | 10/2015 |
| WO | WO 2015/162971 A1 | 10/2015 |
| WO | WO 2015/162983 A1 | 10/2015 |

* cited by examiner

*Primary Examiner* — Hung Q Nguyen
(74) *Attorney, Agent, or Firm* — Oblon, McClelland, Maier & Neustadt, L.L.P.

(57) ABSTRACT

Where a relationship between maximum heat release rate timing and a first combustion period length (that is, a reference relationship) in the case where an engine rotation speed of a spark-ignition internal combustion engine is a selected speed and a valve opening characteristic of an intake valve is a reference characteristic is expressed by the function are $f=f(\theta dQpeak)$ where $\theta dQpeak$ denotes the maximum heat release rate timing and aref denotes the first combustion period length, when the valve opening characteristic of the intake valve changes to a specific characteristic from this state, a first combustion period length for selected maximum heat release rate timing is estimated on the basis of the mathematical expression $a=f(\theta 2)+\Delta a1$ where $\theta 2$ denotes the selected maximum heat release rate timing and a denotes the first combustion period length.

4 Claims, 28 Drawing Sheets

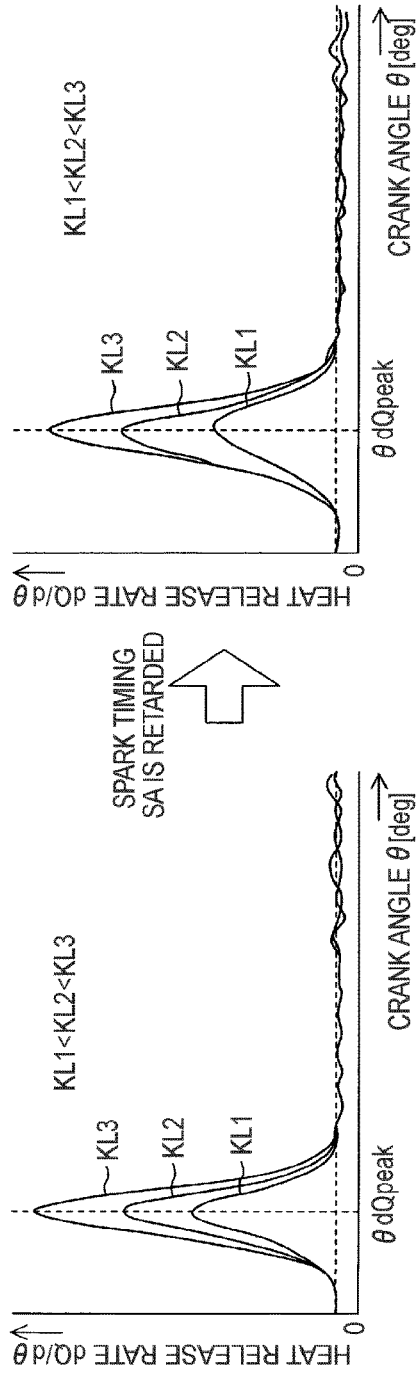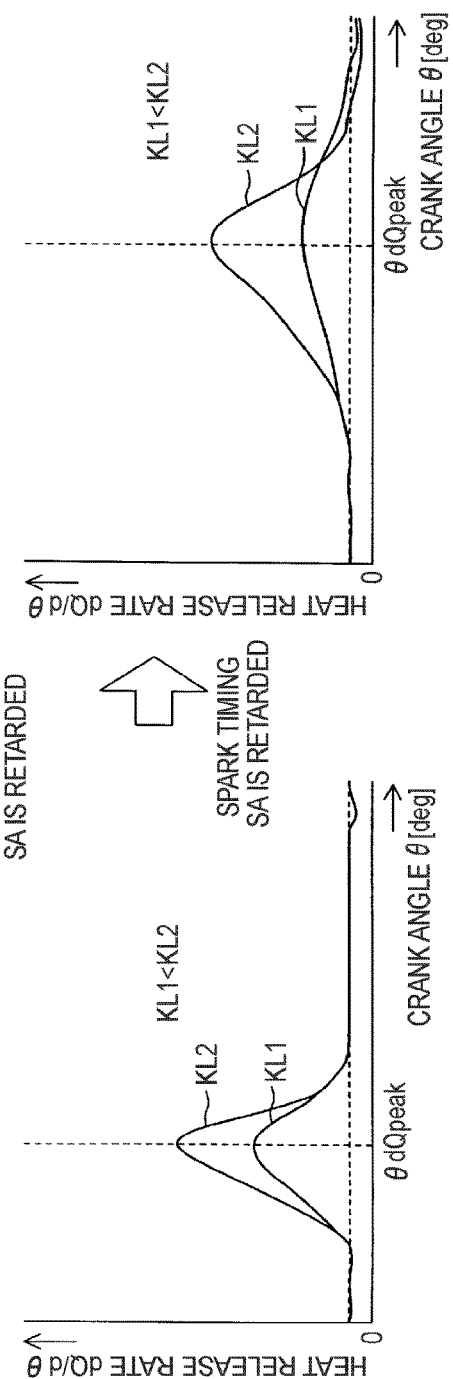

COMBUSTION STATE ESTIMATION METHOD

INCORPORATION BY REFERENCE

The disclosure of Japanese Patent Application No. 2015-037160 filed on Feb. 26, 2015 including the specification, drawings and abstract is incorporated herein by reference in its entirety.

BACKGROUND OF THE INVENTION

1. Field of the Invention

The invention relates to a combustion state estimation method that estimate the length of a first combustion period (first combustion period length) regarding combustion of fuel in an internal combustion engine as one of parameters that indicate a combustion state.

2. Description of Related Art

Various techniques for estimating changes in the amount (heat release amount, heat generation amount) Q of heat that is generated as a result of combustion of fuel in a combustion chamber have been suggested in order to estimate a combustion state of fuel in an internal combustion engine. Particularly, changes in heat release rate (dQ/dθ) in a crank angle (that is, a heat release rate waveform) are important in estimating a combustion state of the internal combustion engine. The heat release rate dQ/dθ is defined as a heat release amount [J/CA] per unit crank angle with respect to rotation of a crankshaft.

The Wiebe function is a function that defines the relationship between various variables and a heat release rate, and is well known as one of effective functions for estimating a heat release rate. Various variables that are used in the Wiebe function are, for example, a shape parameter, an efficiency, an ignition delay period, and the like. Japanese Patent Application Publication No. 2007-177654 (JP 2007-177654 A) describes a technique for determining these variables on the basis of parameters that indicate an engine operating state (for example, spark timing, engine rotation speed, load factor, air-fuel ratio, and the like).

JP 2007-177654 A further describes that it is possible to estimate a first combustion period on the basis of the Wiebe function. The first combustion period is a period from the ignition timing of fuel in a spark-ignition internal combustion engine to timing at which the release rate of heat (heat release rate dQ/dθ) resulting from combustion of the fuel is maximum (that is, maximum heat release rate timing). The length (crank angle width) of the first combustion period is also referred to as first combustion period length. The first combustion period length is one of important parameters in estimating the combustion state of the internal combustion engine.

However, the first combustion period length significantly changes in response to the valve opening characteristic of an intake valve (for example, a characteristic value regarding a period during which the intake valve is open, which is determined by intake valve phase angle, intake valve operating angle, intake valve opening timing, intake valve closing timing, and the like (described later). This is inferably due to the fact that the strength of a disturbance of air stream in a cylinder (combustion chamber) changes when the valve opening characteristic of the intake valve is changed and, as a result, combustion speed changes.

Therefore, if the first combustion period length is estimated by utilizing the Wiebe function, but when the valve opening characteristic of the intake valve changes, it is required to determine the variables of the Wiebe function for various engine operating state parameters again. In addition, when the first combustion period length is acquired with actual measurement, an enormous amount of experiments need to be carried out for various engine operating states each time the valve opening characteristic of the intake valve is changed. In addition, even when the first combustion period length is estimated by the use of a model suggested by the applicant (model expression) described in this specification, it is similarly required to identify various parameters again each time the valve opening characteristic of the intake valve changes. That is, it is required to expend extremely large amounts of time and effort in order to accurately acquire a first combustion period length for each of various valve opening characteristics of the intake valve.

SUMMARY OF THE INVENTION

The invention provides a combustion state estimation method that is able to efficiently estimate a first combustion period length of an internal combustion engine of which the valve opening characteristic of an intake valve can be variously changed.

The inventor made a close study of how the first combustion period length changes in the case where the valve opening characteristic of the intake valve changes. Hereinafter, the results of the study will be described.

FIG. 1 is a graph that schematically shows the actually measured results of the maximum heat release rate timing θdQpeak and first combustion period length a for various intake valve phase angles INVT in a first case where the engine rotation speed is a predetermined speed (constant value) and the intake valve operating angle VCAM is a predetermined angle (constant value).

The maximum heat release rate timing θdQpeak is expressed as a crank angle θ[deg], and the first combustion period length a is expressed as a crank angle width [CA]. The units deg and CA each indicate a crank angle of 1° where an angle of one rotation of a crankshaft is 360°. Generally, deg is used when a specific crank angle is indicated, and CA is used when the width of crank angle is indicated.

The intake valve operating angle VCAM and the intake valve phase angle INVT will be described with reference to FIG. 2A and FIG. 2B. FIG. 2A shows the relationship between a crank angle θ and an intake valve lift. FIG. 2B is a view that shows a crank angle from an intake top dead center to a compression top dead center by circle and that overlappingly shows a period during which the intake valve is open (that is, an intake valve opening period from intake valve opening timing IVO to intake valve closing timing IVC) on the circle. In FIG. 2A and FIG. 2B, a valve opening characteristic (hereinafter, referred to as Characteristic A for the sake of convenience of description) indicated by the continuous line Cr and a valve opening characteristic (hereinafter, referred to as Characteristic B for the sake of convenience of description) indicated by the dashed line Cx have the same intake valve operating angle VCAM, and have mutually different intake valve phase angles IN VT. The intake valve closing timing IVC is expressed as a crank angle [ABDCdeg] after an intake bottom dead center.

As is understood from FIG. 2A and FIG. 2B, the intake valve operating angle VCAM is a crank angle width corresponding to a period from the intake valve opening timing IVO to the intake valve closing timing IVC. In FIG. 2A and FIG. 2B, the intake valve operating angle VCAM of Characteristic A and the intake valve operating angle VCAM of Characteristic B each are a predetermined value (=VC1).

The intake valve phase angle INVT is a crank angle width that indicates how much the crank angle at which the center between the intake valve opening timing IVO and the intake valve closing timing IVC is positioned (that is, the crank angle that indicates the center of an intake valve opening period) is advanced with respect to a reference crank angle. The reference crank angle is the crank angle at which the center between the intake valve opening timing IVO and the intake valve closing timing IVC is positioned in the case where the intake valve opening period is set to the most retarded side within an operation range of an intake valve controller. Therefore, where the intake valve phase angle INVT in Characteristic A is zero (that is, Characteristic A is such a characteristic that the center of the intake valve opening period is set to a most retarded value (=vtr)) and the center of the intake valve opening period of Characteristic B is a value vtx, the intake valve phase angle INVT of Characteristic B is |vtr−vtx|.

Therefore, as shown in FIG. 2A and FIG. 2B, in the case where the intake valve operating angle VCAM is the constant value VC1, when the intake valve phase angle INVT is a crank angle θs, the intake valve opening timing IVO is advanced from the most retarded intake valve opening timing IVOr to the intake valve opening timing IVOx by the crank angle θs, and the intake valve closing timing IVC is advanced from the most retarded intake valve closing timing IVCr to the intake valve closing timing IVCx by the crank angle θs.

Referring back to FIG. 1, the continuous line Cr indicates the relationship between the maximum heat release rate timing θdQpeak and the first combustion period length a in the case where the intake valve phase angle INVT is the reference phase angle INVTr. Here, the reference phase angle INVTr is set to a predetermined value larger than zero. The alternate long and short dashes line Cs indicates the relationship between the maximum heat release rate timing θdQpeak and the first combustion period length a in the case where the intake valve phase angle INVT is a phase angle different from the reference phase angle INVTr (for example, a retard-side value smaller than the reference phase angle INVTr) INVTs. The alternate long and two short dashes line Cd indicates the relationship between the maximum heat release rate timing θdQpeak and the first combustion period length a in the case where the intake valve phase angle INVT is a phase angle different from any of the reference phase angle INVTr and the phase angle INVTs (for example, an advance-side value larger than the reference phase angle INVTr) INVTd.

As is understood from this graph, the inventor found that, in the case where the engine rotation speed is kept at a predetermined speed and the intake valve operating angle VCAM is kept at a predetermined angle, when the intake valve phase angle INVT changes from a first phase angle (INVTr) to a second phase angle (INVTs or INVTd), the first combustion period length a changes by a predetermined value (for example, Δa1 or Δa2) irrespective of the maximum heat release rate timing θdQpeak. In other words, the inventor found that, in the case where the engine rotation speed is kept at a predetermined speed and the intake valve operating angle VCAM is kept at a predetermined angle, when the intake valve phase angle INVT changes, a curve that indicates the relationship between the maximum heat release rate timing θdQpeak and the first combustion period length a is translated in the direction in which the first combustion period length a changes (any one of an increasing direction and a reducing direction, that is, the Y-axis direction in FIG. 1).

More specifically, when the intake valve phase angle INVT was the reference phase angle INVTr, the first combustion period length a at the time when the maximum heat release rate timing θdQpeak is the reference value θ1 was ar1 (see point Pr1), and the first combustion period length a at the time when the maximum heat release rate timing θdQpeak is the selected value θ2 was ar2 (see point Pr2). In addition, when the intake valve phase angle INVT was a predetermined phase angle different from the reference phase angle INVTr (retard-side INVTs smaller than INVTr or advance-side INVTd larger than INVTr), the first combustion period length a at the time when the maximum heat release rate timing θdQpeak is the reference value θ1 was ad1 (see point Pa1), and the first combustion period length a at the time when the maximum heat release rate timing θdQpeak is the selected value θ2 was ad2 (see point Pa2). The inventor found that the mathematical expression (1A) described below holds for all the selected values θ2. In addition, the inventor found that, as will be described later, the mathematical expression (1A) similarly holds for another engine rotation speed NE and another intake valve operating angle VCAM as long as those do not change.

$$(ad1-ar1)=(ad2-ar2)=\Delta a1 \quad (1A)$$

Therefore, the inventor obtained the following findings 1. The relationship (that is, the reference relationship) between the maximum heat release rate timing θdQpeak and the first combustion period length aref in the case where the engine rotation speed NE is a selected speed NE0, the intake valve operating angle VCAM is a selected operating angle VCAM0 and the intake valve phase angle INVT is a reference phase angle INVTr is expressed by the function aref =f(θdQpeak). At this time, when it is assumed that the first combustion period length as(θ1) at the time when the engine rotation speed NE is the selected speed NE0, the intake valve operating angle VCAM is the selected operating angle VCAM0, the intake valve phase angle INVT is the predetermined phase angle INVTs and the maximum heat release rate timing θdQpeak is a selected value (selected reference value) θ1 is ad1, the first combustion period length as(θ2) at the time when the engine rotation speed NE is the selected speed NE0, the intake valve operating angle VCAM is the selected operating angle VCAM0, the intake valve phase angle INVT is the predetermined phase angle INVTs and the maximum heat release rate timing θdQpeak is a selected value θ2 is allowed to be obtained by the use of the following mathematical expression (1B).

$$as(\theta 2)=f(\theta 2)+\Delta a1=f(\theta 2)+(ad1-ar1)=f(\theta 2)-(ar1-ad1)=f(\theta 2)+\{ad1-f(\theta 1)\} \quad (1B)$$

The value (ad1−ar1) is also referred to as first differential value for the sake of convenience. The value (ar1−ad1) is also referred to as second differential value for the sake of convenience. Therefore, the above-described mathematical expression (1B) is a mathematical expression for estimating the first combustion period length as(θ2) by adding the first differential value to f(θ2), and is a mathematical expression for estimating the first combustion period length as(θ2) by subtracting the second differential value from f(θ2).

Therefore, when the above-described reference relationship (aref —f(θdQpeak)) has been obtained with actual measurement or on the basis of estimation using a model, or the like, and, in addition, the first combustion period length ad1 has been obtained with actual measurement, or the like, it is possible to estimate the relationship between the maximum heat release rate timing θdQpeak and the first combustion period length a as in the case where the intake valve phase angle INVT is the phase angle INVTs from the above-described mathematical expression (1B).

On the other hand, FIG. 3 is a graph that schematically shows the actually measured results of the maximum heat release rate timing θdQpeak and first combustion period length a for various intake valve operating angles VCAM in the case where the engine rotation speed is a predetermined speed (constant value) and the valve closing timing IVC of the intake valve is a predetermined crank angle (constant value).

For the sake of easy understanding of the preconditions of the results shown in FIG. 3, FIG. 4A shows the relationship between the crank angle θ and the intake valve lift in the case where the intake valve operating angle VCAM is set to the valve operating angle VCr (see the continuous line Cr) and in the case where the intake valve operating angle VCAM is set to the valve operating angle VCs smaller than the valve operating angle VCr (see the dashed line Cx) while the intake valve closing timing IVC is kept at the constant crank angle IVCr. In addition, FIG. 4B as well as FIG. 2B shows the valve opening periods of the intake valve corresponding to the continuous line Cr and the dashed line Cx in FIG. 4A by the continuous line Cr and the dashed line Cx. As is understood from FIG. 4A and FIG. 4B, in the case where the valve closing timing IVC of the intake valve is a predetermined crank angle (constant value), when the intake valve operating angle VCAM changes, at least the valve opening timing IVO of the intake valve changes, and, actually, the intake valve lift and the intake valve phase angle INVT also change.

Referring back to FIG. 3, the continuous line Lr indicates the relationship between the maximum heat release rate timing θdQpeak and the first combustion period length a in the case where the intake valve operating angle VCAM is the reference valve operating angle VCAMr. The alternate long and short dashes line Ls indicates the relationship between the maximum heat release rate timing θdQpeak and the first combustion period length a in the case where the intake valve operating angle VCAM is a valve operating angle VCAMs different from the reference valve operating angle VCAMr (for example, a valve operating angle smaller than the reference valve operating angle VCAMr). The alternate long and two short dashes line Ld indicates the relationship between the maximum heat release rate timing θdQpeak and the first combustion period length a in the case where the intake valve operating angle VCAM is a valve operating angle VCAMd different from any of the reference valve operating angle VCAMr and the valve operating angle VCAMs (for example, a valve operating angle larger than the reference valve operating angle VCAMr).

As is understood from this graph, the inventor found that, in the case where the engine rotation speed is kept at a predetermined speed and the intake valve closing timing IVC is kept at a predetermined crank angle, when the intake valve operating angle VCAM changes from a first valve operating angle (VCAMr) to a second valve operating angle (VCAMs or VCAMd), the first combustion period length a changes by a predetermined value (for example, Δa3 or Δa4) irrespective of the maximum heat release rate timing θdQpeak. In other words, the inventor found that, in the case where the engine rotation speed is kept at a predetermined speed and the intake valve closing timing IVC is kept at a predetermined crank angle, when the intake valve operating angle VCAM changes, a curve that indicates the relationship between the maximum heat release rate timing θdQpeak and the first combustion period length a is translated in the direction in which the first combustion period length a changes (any one of an increasing direction and a reducing direction, that is, the Y-axis direction in FIG. 3).

More specifically, when the intake valve operating angle VCAM was the reference valve operating angle VCAMr, the first combustion period length a at the time when the maximum heat release rate timing θdQpeak is a reference value θ3 was ar3 (see point Pr3), and the first combustion period length a at the time when the maximum heat release rate timing θdQpeak is a selected value θ4 was ar4 (see point Pr4). In addition, when the intake valve operating angle VCAM was a predetermined valve operating angle different from the reference valve operating angle VCAMr (a valve operating angle VCAMd larger than VCAMr or a valve operating angle VCAMs smaller than the reference valve operating angle VCAMr), the first combustion period length a at the time when the maximum heat release rate timing θdQpeak is the reference value θ3 was ad3 (see point Pa3), and the first combustion period length a at the time when the maximum heat release rate timing θdQpeak is the selected value θ4 was ad4 (see point Pa4). The inventor found that the following mathematical expression (2A) holds for all the selected values θ4. In addition, the inventor found that, as will be described later, the mathematical expression (2A) similarly holds for another engine rotation speed NE and another intake valve closing timing IVC as long as those do not change.

$$(ad3-ar3)=(ad4-ar4)=\Delta a3 \qquad (2A)$$

Therefore, the inventor obtained the following findings 2. The relationship (that is, the reference relationship) between the maximum heat release rate timing θdQpeak and the first combustion period length aref in the case where the engine rotation speed NE is the selected speed NE0, the intake valve closing timing IVC is selected valve closing timing IVC0 and the intake valve operating angle VCAM is the reference valve operating angle VCAMr is expressed by the function aref=g(θdQpeak). At this time, when it is assumed that the first combustion period length as(θ3) at the time when the engine rotation speed NE is the selected speed NE0, the intake valve closing timing IVC is the selected valve closing timing IVC0, the intake valve operating angle VCAM is the predetermined operating angle VCAMs and the maximum heat release rate timing θdQpeak is a selected value (selected reference value) θ3 is ad3, the first combustion period length as(θ4) at the time when the engine rotation speed NE is the selected speed NE0, the intake valve closing timing IVC is the selected valve closing timing IVC0, the intake valve operating angle VCAM is the predetermined operating angle VCAMs and the maximum heat release rate timing θdQpeak is a selected value θ4 is allowed to be obtained by the use of the following mathematical expression (2B).

$$as(\theta 4)=g(\theta 4)+\Delta a3=g(\theta 4)+(ad3-ar3)=g(\theta 4)-(ar3-ad3)=g(\theta 4)+\{ad3-g(\theta 3)\} \qquad (2B)$$

The value (ad3−ar3) is also referred to as first differential value for the sake of convenience. The value (ar3−ad3) is also referred to as second differential value for the sake of convenience. Therefore, the above-described mathematical expression (2B) is a mathematical expression for estimating the first combustion period length as(θ4) by adding the first differential value to g(θ4), and is a mathematical expression for estimating the first combustion period length as(θ4) by subtracting the second differential value from g(θ4).

Therefore, when the above-described reference relationship (aref =g(θdQpeak)) has been obtained with actual measurement or on the basis of estimation using a model, or the like, and, in addition, the first combustion period length ad3 has been obtained with actual measurement, or the like, it is possible to estimate the relationship between the maximum heat release rate timing θdQpeak and the first combustion period length as in the case where the intake valve operating angle VCAM is the valve operating angle VCAMs from the above-described mathematical expression (2B).

Incidentally, as is understood from the description made with reference to FIG. 2A, FIG. 2B, FIG. 4A and FIG. 4B and the following relational expressions (*1), (*2), there is such a relationship that, when any two of the intake valve closing timing (IVC), the intake valve opening timing (IVO), the intake valve operating angle (VCAM) and the intake valve phase angle (INVT) are determined, the remaining two are automatically determined. Here, the intake valve opening timing IVO is also expressed as a crank angle [ABDCdeg] after the intake bottom dead center.

$$(IVC-IVO)=VCAM \quad (*1)$$

$$(IVC+IVO)/2=Vtr-INVT \quad (*2)$$

Therefore, for example, when the valve closing timing (IVC) of the intake valve and the intake valve operating angle (VCAM) in one of the valve opening characteristics of the intake valve are respectively the same as the valve closing timing (IVC) of the intake valve and the intake valve operating angle (VCAM) in another one of the valve opening characteristics of the intake valve, it may be regarded that both the valve opening characteristics of the intake valve are equal to each other. In other words, the specific valve opening characteristic may be different from the reference valve opening characteristic in at least one of the valve closing timing (IVC) of the intake valve and the intake valve operating angle (VCAM). Alternatively, the specific valve opening characteristic may be different from the reference valve opening characteristic in at least one of the intake valve phase angle (INVT) and the intake valve operating angle (VCAM).

In an ordinary internal combustion engine that opens or closes an intake valve by the use of an intake camshaft and a cam, a maximum value (maximum valve lift) of a lift (IVLift) of the intake valve is a certain specific value when the intake valve operating angle (VCAM) is determined. Thus, the specific valve opening characteristic may be different from the reference valve opening characteristic in at least one of the valve closing timing (IVC) of the intake valve and the maximum valve lift of the intake valve. Alternatively, the specific valve opening characteristic may be different from the reference valve opening characteristic in at least one of the intake valve phase angle (INVT) and the maximum valve lift of the intake valve.

The above-described findings 1 mean that the curve that expresses the relationship between the maximum heat release rate timing θdQpeak and the first combustion period length a is translated in the direction in which the first combustion period length a increases or reduces between the following Case 1 and the following Case 2.
Case 1) Intake valve phase angle INVT=A1
Intake valve operating angle VCAM=B1
Intake valve closing timing IVC=C1
Case 2) Intake valve phase angle INVT=A2
Intake valve operating angle VCAM=B1
Intake valve closing timing IVC=C2

The above-described findings 2 mean that, when the intake valve operating angle VCAM is set to an appropriate value, the curve that expresses the relationship between the maximum heat release rate timing θdQpeak and the first combustion period length a is translated in the direction in which the first combustion period length a increases or reduces between the above-described Case 2 and the following Case 3.
Case 3) Intake valve phase angle INVT=A1
Intake valve operating angle VCAM=B2
Intake valve closing timing IVC=C2

Therefore, it means that the curve that expresses the relationship between the maximum heat release rate timing θdQpeak and the first combustion period length a is translated in the direction in which the first combustion period length a increases or reduces between the above-described Case 1 and the above-described Case 3 as well (that is, when the intake valve phase angle INVT is kept at the constant value A1 and the intake valve operating angle VCAM changes (as a result, the intake valve closing timing IVC changes) as well).

From above, the inventor obtained findings 3 that, when the rotation speed of the engine is a constant speed, the curve that expresses the relationship between the maximum heat release rate timing θdQpeak and the first combustion period length a is translated by a constant amount that is determined depending on the reference valve opening characteristic and the specific valve opening characteristic in the direction in which the first combustion period length a increases or reduces.

The combustion state estimation method according to the invention made on the basis of the above-described findings 1 to 3 is a combustion state estimation method that acquires a relationship between maximum heat release rate timing and a first combustion period length in a reference state as a reference relationship with, for example, estimation based on the Weibe function and a model described in the specification or with actual measurement, the reference state being a state where a rotation speed of a spark-ignition internal combustion engine is a predetermined reference rotation speed and a valve opening characteristic of an intake valve of the engine is set to a predetermined reference valve opening characteristic, and that estimates a relationship between the maximum heat release rate timing and the first combustion period length in a specific state on the basis of the reference relationship, the specific state being a state where the rotation speed of the engine is the reference rotation speed and the valve opening characteristic of the intake valve is a specific valve opening characteristic different from the reference valve opening characteristic. The combustion state estimation method further includes the following steps. However, the order in which the steps described below are executed is not limited as long as there is no contradiction.

The combustion state estimation method includes: a step (first step) of acquiring the first combustion period length at the time when the maximum heat release rate timing is predetermined first timing in the reference state as a first reference period length on the basis of the reference relationship or with actual measurement; a step (second step) of acquiring the first combustion period length at the time when the maximum heat release rate timing is the first timing in the specific state as a first specific period length with actual measurement; a step (third step) of acquiring a first differential value (for example, Δa1=ad1−ar1 or Δa3=ad3−ar3) by subtracting the first reference period length from the first specific period length or acquiring a second differential value (for example, $-\Delta a1=ar1-ad1$ or $-\Delta a3=ar3-ad3$) by subtracting the first specific period length from the first reference period length; a step (fourth step) of acquiring the first combustion period length at the time when the maximum heat release rate timing is second timing different from the first timing in the reference state as a second reference period length on the basis of the reference relationship; and a step (fifth step) of estimating the first combustion period length at the time when the maximum heat release rate timing is the second timing in the specific state by adding the first differential value to the second reference period length (for example, $f(\theta 2)+(ad1-ar1)$) or subtracting the second differential value from the second reference period length (for example, $f(\theta 2)-(ar1-ad1)$).

With this method, in the case where the rotation speed of the engine is the reference rotation speed, when the reference relationship and the first specific period length in the case where the valve opening characteristic of the intake valve is the specific valve opening characteristic are acquired, it is possible to immediately estimate the relationship between the maximum heat release rate timing and the first combustion period length in the case where the valve opening characteristic of the intake valve has changed to the specific valve opening characteristic. Therefore, it is possible to estimate the first combustion period length for the maximum heat release rate timing at each of various valve opening characteristics of the intake valve with extremely small time and effort.

A more specific example of the reference valve opening characteristic and the specific valve opening characteristic is as follows. As is understood from FIG. 1, FIG. 2A and FIG. 2B, the reference valve opening characteristic may be such a characteristic that the intake valve operating angle (VCAM) is a predetermined reference valve operating angle and an intake valve phase angle (INVT) that is a crank angle difference between a predetermined reference crank angle and a crank angle that indicates a center between valve opening timing of the intake valve and the valve closing timing of the intake valve is a predetermined reference phase angle, and the specific valve opening characteristic may be such a characteristic that the intake valve operating angle (VCAM) is the reference valve operating angle and the intake valve phase angle (INVT) is a specific phase angle different from the reference phase angle.

Similarly, as is understood from FIG. 3, FIG. 4A and FIG. 4B, the reference valve opening characteristic may be such a characteristic that the valve closing timing (IVC) of the intake valve is predetermined reference valve closing timing and the intake valve operating angle (VCAM) is a predetermined reference valve operating angle, and the specific valve opening characteristic may be such a characteristic that the valve closing timing (IVC) of the intake valve is the reference valve closing timing and the intake valve operating angle (VCAM) is a specific valve operating angle different from the reference valve operating angle.

Other features and associated advantages are easily understood from embodiments of the invention described with reference to the accompanying drawings. In the above description, for the sake of understanding of the invention, specific symbols and signs are used in the function that expresses the reference relationship, the first differential value, the second differential value, and the like; however, these do not limit the invention.

BRIEF DESCRIPTION OF THE DRAWINGS

Features, advantages, and technical and industrial significance of exemplary embodiments of the invention will be described below with reference to the accompanying drawings, in which like numerals denote like elements, and wherein:

FIG. 25A to FIG. 25D are graphs, each of which shows heat release rate waveforms acquired in a plurality of mutually different engine operating states of which only load factors are different from one another among engine operating state parameters except spark timing and that overlappingly shows the heat release rate waveforms of which the spark timings are adjusted such that maximum heat release rate timings coincide with one another.

DETAILED DESCRIPTION OF EMBODIMENTS

Hereinafter, a combustion state estimation method according to an embodiment of the invention (hereinafter, also simply referred to as embodiment method) will be described with reference to the accompanying drawings. A simulation apparatus that uses the embodiment method is also hereinafter simply referred to as embodiment apparatus.

The embodiment apparatus is implemented by a computer including a CPU, a memory, and the like.

Figure 5:
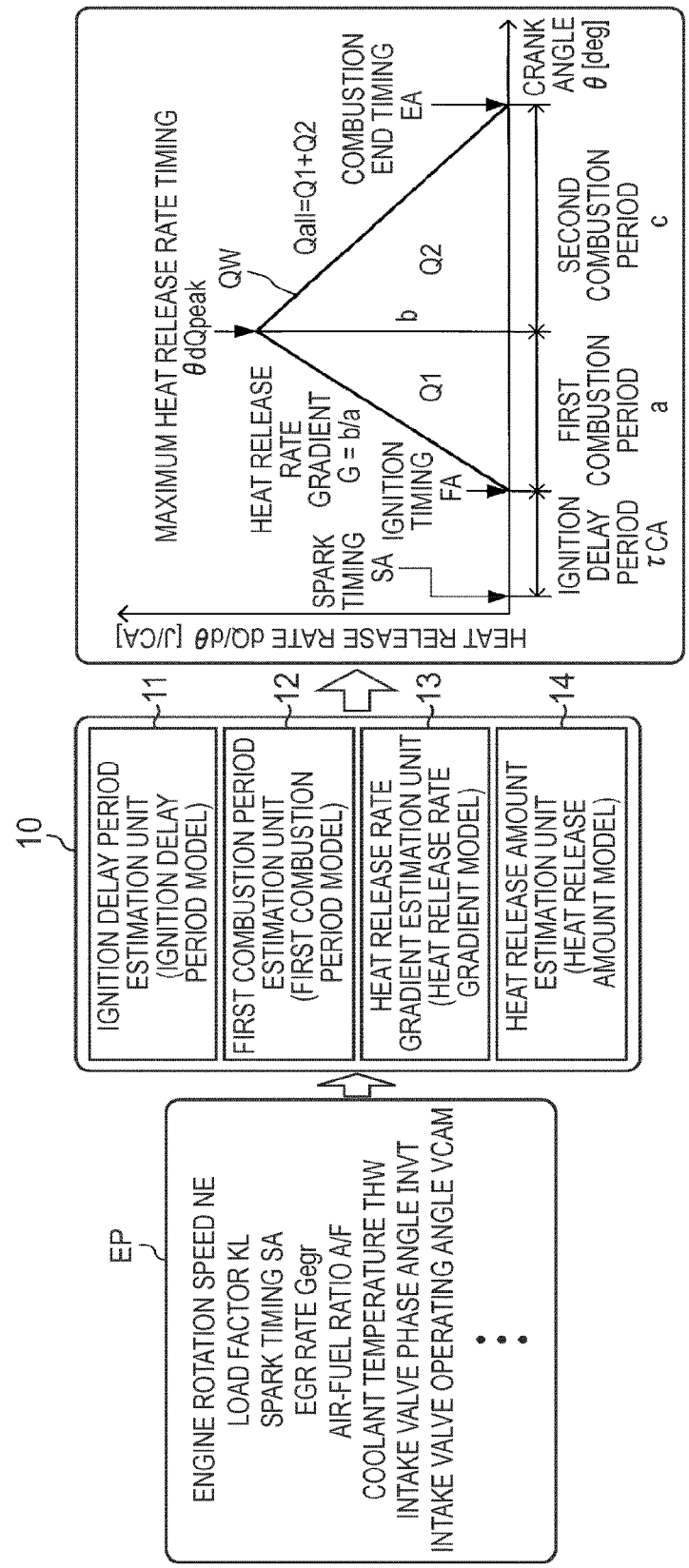
FIG. 5 is a view that shows the configuration of an apparatus (simulator) according to an embodiment of the invention.

The embodiment apparatus (simulation apparatus) 10 of which the schematic configuration is shown in FIG. 5 estimates a combustion state of a known gasoline port-injection piston-reciprocating spark-ignition multi-cylinder internal combustion engine (hereinafter, also simply referred to as engine) with the use of the embodiment method. More specifically, the embodiment apparatus 10 receives parameters (hereinafter, also referred to as engine operating state parameters) EP that indicate an operating state of the intended internal combustion engine, and performs computation on the basis of the received engine operating state parameters, thus generating a waveform (hereinafter, also simply referred to as heat release rate waveform) QW that simulates a heat release rate $dQ/d\theta$ for a crank angle $\theta$. The heat release rate waveform QW favorably expresses the combustion state of fuel (air-fuel mixture) in the engine.

The engine operating state parameters EP include an engine rotation speed NE, a load factor KL, spark timing SA, an EGR rate Gegr, an air-fuel ratio A/F of air-fuel mixture that is supplied to the engine, a coolant temperature THW of the engine, an intake valve phase angle INVT, an intake valve operating angle VCAM, and the like. As shown in FIG. 5, the embodiment apparatus 10 estimates a heat release rate waveform such that the heat release rate waveform QW is substantially a triangle.

Figure 6:
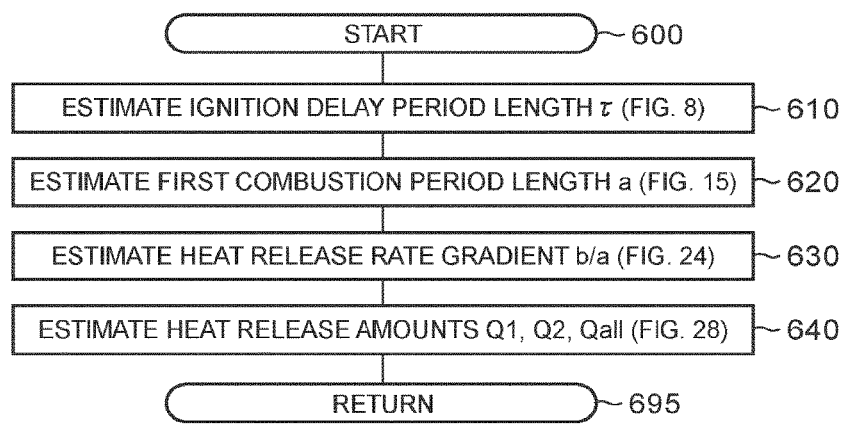
FIG. 6 is a flowchart that shows steps that are executed by the apparatus (embodiment apparatus) shown in FIG. 5 (that is, embodiment method)

In order to estimate the heat release rate waveform QW, the embodiment apparatus 10 includes an ignition delay period estimation unit (ignition delay period model) 11, a first combustion period estimation unit (first combustion period model) 12, a heat release rate gradient estimation unit (heat release rate gradient model) 13 and a heat release amount estimation unit (heat release amount model) 14. The functions of these estimation units (models) 11 to 14 are actually implemented such that the CPU executes programs (instructions). Therefore, as shown in FIG. 6, the embodiment apparatus 10 estimates the length $\tau$ of an ignition delay period (ignition delay period length), the length a of a first combustion period (first combustion period length), a heat release rate gradient b/a, heat release amounts (Q1, Q2 and Qa11), and the like, by sequentially implementing the functions of the estimation units 11 to 14 by the use of the CPU (that is, executing the processes of step 610 to step 640). Hereinafter, these estimation units will be individually described.

1. Ignition Delay Period Estimation Unit (Outline of Ignition Delay Period Estimation Unit)

Figure 7:
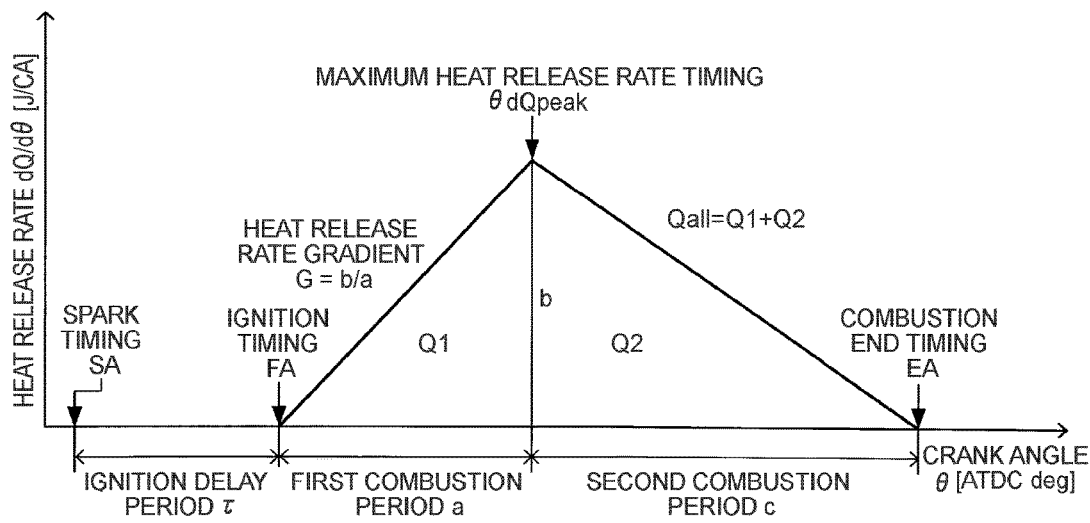
FIG. 7 is a graph that shows an example of a heat release rate waveform that is estimated by the embodiment apparatus.

As shown in FIG. 7, the ignition delay period is a period from spark timing SA at which spark is generated from an ignition plug to ignition timing FA at which fuel of air-fuel mixture formed in a combustion chamber actually starts combustion. That is, the ignition delay period is a period from the spark timing SA at which spark is discharged between the electrodes of the ignition plug to the ignition timing FA at which a flame kernel produced by the spark grows and explosive combustion starts. The ignition delay period length $\tau$ is the length of the ignition delay period. The unit of the ignition delay period length $\tau$ is crank angle [CA]; however, the ignition delay period length $\tau$ may be calculated as a period in ms for the sake of convenience of the model.

The ignition timing FA is defined as the timing at which the heat release rate $dQ/d\theta$ reaches a predetermined threshold $dqd\theta th$ (for example, 1 [J/CA]) after the spark timing SA. However, the ignition timing FA may be defined as the timing at which the heat release rate $dQ/d\theta$ becomes larger than 0 [J/CA] after the spark timing SA or may be defined as the timing at which a heat release amount after the spark timing SA reaches a heat release amount that is a predetermined percentage (for example, 5%) of a total heat release amount. Other than the above, the ignition timing FA may be the timing set in accordance with a general definition that is recognized by persons skilled in the art.

The ignition delay period estimation unit 11 estimates the ignition delay period length τ [ms] by the use of any one of the following mathematical expression (1) and mathematical expression (2). However, the ignition delay period length τ that is estimated by the use of the mathematical expression (1) or the mathematical expression (2) is the ignition delay period length τ in the case where all the following conditions are satisfied. Grounds for allowing the ignition delay period length τ to be accurately estimated on the basis of these mathematical expressions will be described later.

(Condition τ1) The air-fuel ratio A/F of air-fuel mixture that is subjected to combustion is a stoichiometric air-fuel ratio (for example, 14.6).

(Condition τ2) The EGR rate Gegr is zero. That is, external EGR is not carried out.

(Condition τ3) The coolant temperature THW is higher than or equal to a coolant temperature threshold Tth (for example, 80° C.) that indicates a complete engine warm-up end. The condition τ3 is a condition that the engine has been completely warmed up, so the temperature of lubricating oil for the engine may be used in determination as to the condition τ3 instead of the coolant temperature THW.

(Condition τ4) The valve opening characteristic of each intake valve (intake valve opening timing IVO, intake valve closing timing IVC, an intake valve operating angle VCAM, an intake valve phase angle INVT, the maximum value of an intake valve lift IVLift, and the like) is set to a reference characteristic of each intake valve (intake valve reference characteristic). That is, the intake valve opening timing IVO is set to reference valve opening timing IVOr, the intake valve closing timing IVC is set to reference valve closing timing IVCr, the intake valve operating angle VCAM is set to a reference valve operating angle VCAMr, the intake valve phase angle INVT is set to a reference phase angle INVTr, and the maximum value of the intake valve lift IVLift is set to a reference maximum value.

(Condition τ5) The valve opening characteristic of each exhaust valve (exhaust valve opening timing EVO, exhaust valve closing timing EVC, an exhaust valve phase angle EXVT, the maximum value of an exhaust valve lift EVLift, and the like) is set to a reference characteristic of each exhaust valve. That is, the exhaust valve opening timing EVO, the exhaust valve closing timing EVC, the exhaust valve phase angle EXVT and the exhaust valve lift EVLift are respectively set to reference values.

The ignition delay period estimation unit 11 estimates the ignition delay period length τ[ms] on the basis of the following mathematical expression (1) when the ignition timing FA is the timing before a compression top dead center (the timing at which the crank angle is a crank angle on an advance side with respect to the compression top dead center). This case is also referred to as BTDC ignition.

$$\tau[ms]=C1\times\rho_{fuel@SA}{}^{\chi}\times NE^{\delta} \quad (1)$$

(in the case of BTDC ignition)

In the mathematical expression (1), C1 denotes a constant adapted in advance by experiment, or the like, ρfuel@SA denotes a fuel density in a cylinder (in a combustion chamber) at the spark timing SA (=In-cylinder fuel amount [mol]/Combustion chamber volume [L] at the spark timing SA), and χ and δ each denote a constant adapted in advance by experiment, or the like. NE is an engine rotation speed (the same applies in this specification).

The ignition delay period estimation unit 11 estimates the ignition delay period length τ[ms] on the basis of the following mathematical expression (2) when the ignition timing FA is set to a point in time after the compression top dead center (the timing at which the crank angle is a crank angle on a retard side with respect to the compression top dead center). This case is also referred to as ATDC ignition.

$$\tau[ms]=C2\times\rho_{fuel@FA}{}^{\phi}\times NE^{\psi} \quad (2)$$

(in the case of ATDC ignition)

In the mathematical expression (2), C2 denotes a constant adapted in advance by experiment, or the like, ρfuel@FA denotes a fuel density in the cylinder at the ignition timing FA (=In-cylinder fuel amount [mol]/Combustion chamber volume [L] at the ignition timing FA), and φ and ψ each denote a constant adapted in advance by experiment, or the like.

Operation of Ignition Delay Period Estimation Unit

Figure 8:
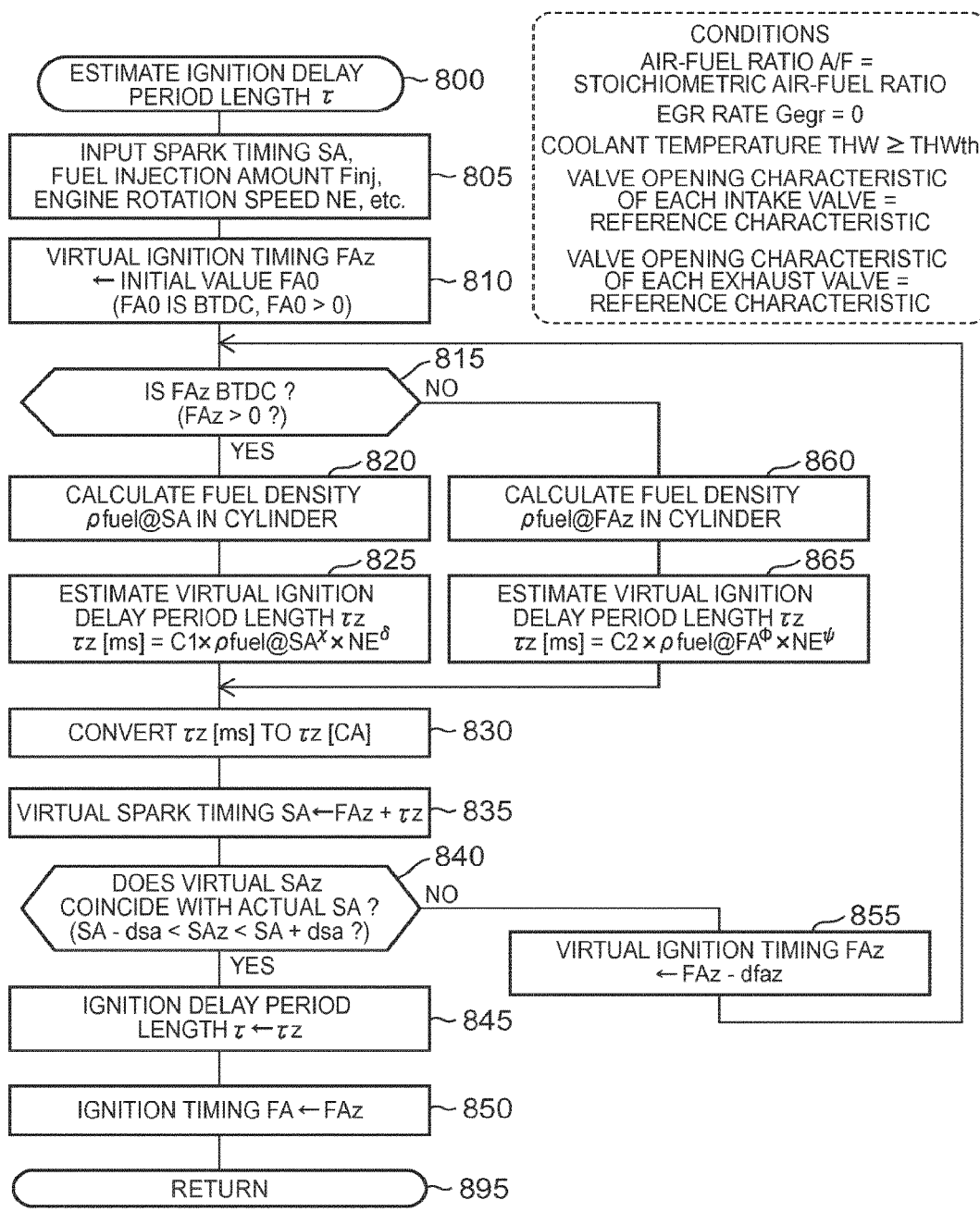
FIG. 8 is a flowchart that shows a routine that is executed by a CPU of the embodiment apparatus.

The CPU estimates the ignition delay period length τ [CA] in accordance with the routine shown by the flowchart in FIG. 8 in order to implement the function corresponding to the ignition delay period estimation unit 11. As a result, the CPU further estimates the ignition timing FA. In the routine shown in FIG. 8, the crank angle is expressed as a crank angle before the compression top dead center (BTDC) (positive value that increases as the crank angle is advanced from the compression top dead center).

The CPU starts the process from step 800, proceeds to step 805, and receives (acquires) various engine operating state parameters, such as spark timing SA, a fuel injection amount Finj and an engine rotation speed NE.

Subsequently, the CPU proceeds to step 810, and sets virtual ignition timing FAz to an initial value FA0. The virtual ignition timing FAz is ignition timing that is virtually (temporarily) set in order to estimate the ignition delay period length τ. The initial value FA0 is a predetermined crank angle before the compression top dead center (BTDC), and is set in advance to a crank angle on a retard side with respect to the spark timing SA and on an advance side with respect to most advanced ignition timing FAad within assumed ignition timing (SA>FA0>FAad).

Subsequently, the CPU proceeds to step 815, and determines whether the virtual ignition timing FAz is the timing before the compression top dead center. When the process proceeds to step 815 for the first time, the virtual ignition timing FAz is the initial value FA0 that is the crank angle before the compression top dead center. Therefore, the CPU makes affirmative determination in step 815, and sequentially executes the processes of step 820 to step 840, which will be described below.

In step 820, the CPU calculates the fuel density ρfuel@SA in the cylinder at the spark timing SA by dividing the fuel injection amount Finj by the cylinder volume (combustion chamber volume) V@SA at the spark timing SA. The combustion chamber volume (cylinder volume) V is uniquely calculated when the crank angle is determined, so the combustion chamber volume V@SA is also immediately calculated. In step 825, the CPU calculates a virtual ignition delay period length ρz [ms] by substituting the fuel density ρfuel@SA in the cylinder and the engine rotation speed NE into the same mathematical expression as the mathematical expression (1).

In step 830, the CPU calculates a virtual ignition delay period length ρz [CA] by converting the unit [ms] of the virtual ignition delay period length τz to the unit [CA] of the crank angle on the basis of the engine rotation speed NE. In step 835, the CPU calculates virtual spark timing SAz [CA] by adding the virtual ignition delay period length τz [CA] to the virtual ignition timing FAz [CA] (see FIG. 7). In step 840, the CPU determines whether the virtual spark timing SAz coincides with the spark timing SA. Specifically, the CPU determines whether the virtual spark timing SAz is larger than a crank angle obtained by subtracting a small positive predetermined crank angle dsa from the spark timing SA and is smaller than a crank angle obtained by adding the predetermined crank angle dsa to the spark timing SA.

When the virtual spark timing SAz coincides with the spark timing SA, it is understood that the virtual ignition timing FAz virtually set in order to calculate the ignition delay period length τ is equal to the actual ignition timing FA. Therefore, when the virtual spark timing SAz coincides with the spark timing SA, the CPU makes affirmative determination in step 840, sequentially executes the processes of step 845 and step 850, which will be escribed below, proceeds to step 895, and then ends the routine.

In step 845, the CPU employs the virtual ignition delay period length τz [CA] as the ignition delay period length τ [CA]. That is, the CPU finally determines the virtual ignition delay period length τz [CA] calculated at this point in time as an estimated ignition delay period length τ [CA]. In step 850, the CPU employs the virtual ignition timing FAz as the ignition timing FA. That is, the CPU finally determines the virtual ignition timing FAz at this point in time as estimated ignition timing (true ignition timing, actual ignition timing) FA.

On the other hand, when the virtual spark timing SAz does not coincide with the spark timing SA at the point in time at which the CPU executes the process of step 840, the CPU makes negative determination in step 840, proceeds to step 855, and then reduces the virtual ignition timing FAz by a small predetermined value dfaz. That is, the virtual ignition timing FAz is changed to a crank angle on a retard side by the small predetermined value dfaz. After that, the CPU proceeds to step 815.

Such processes are repeated, and, when the virtual spark timing SAz coincides with the spark timing SA in a period during which the virtual ignition timing FAz gradually approaches from the initial value FA0 to the compression top dead center, the virtual ignition delay period length τz at that point in time is acquired as the ignition delay period length ti, and the virtual ignition timing FAz at that point in time is acquired as the ignition timing FA.

In contrast, when the virtual spark timing SAz does not coincide with the spark timing SA by the time the virtual ignition timing FAz becomes a negative value (that is, a crank angle after the compression top dead center), and when the CPU proceeds to step 815, the CPU makes negative determination in step 815, and then sequentially executes the processes of step 860 and step 865, which will be described below. After that, the CPU proceeds to step 830 and the following steps.

In step 860, the CPU calculates a fuel density ρfuel@FAz in the cylinder at the virtual ignition timing FAz by dividing the fuel injection amount Finj by the combustion chamber volume V@FAz at the virtual ignition timing FAz. The combustion chamber volume V is uniquely calculated when the crank angle is determined, so the combustion chamber volume V@FAz is also immediately calculated. In step 865, the CPU calculates a virtual ignition delay period length τz [ms] by substituting the fuel density ρfuel@FAz in the cylinder and the engine rotation speed NE into the above-described mathematical expression (2).

As described above, the ignition delay period length ρ [CA] and the ignition timing FA are estimated (acquired). When the ignition timing FA is expressed as a crank angle after the compression top dead center, the sign of the ignition timing FA estimated in step 850 is inverted. That is, the ignition timing FA (ATDCdeg) is-FA (BTDCdeg).

Validity of Ignition Delay Period Estimation Unit

Next, the point that it is possible to accurately estimate the ignition delay period length τ on the basis of the above-described mathematical expression (1) or mathematical expression (2) will be described. That is, the point that the mathematical expression (1) and the mathematical expression (2) are appropriate models as the ignition delay period model will be described.

Regarding the mathematical expression (1) (in the case of BTDC ignition)

Figure 9:
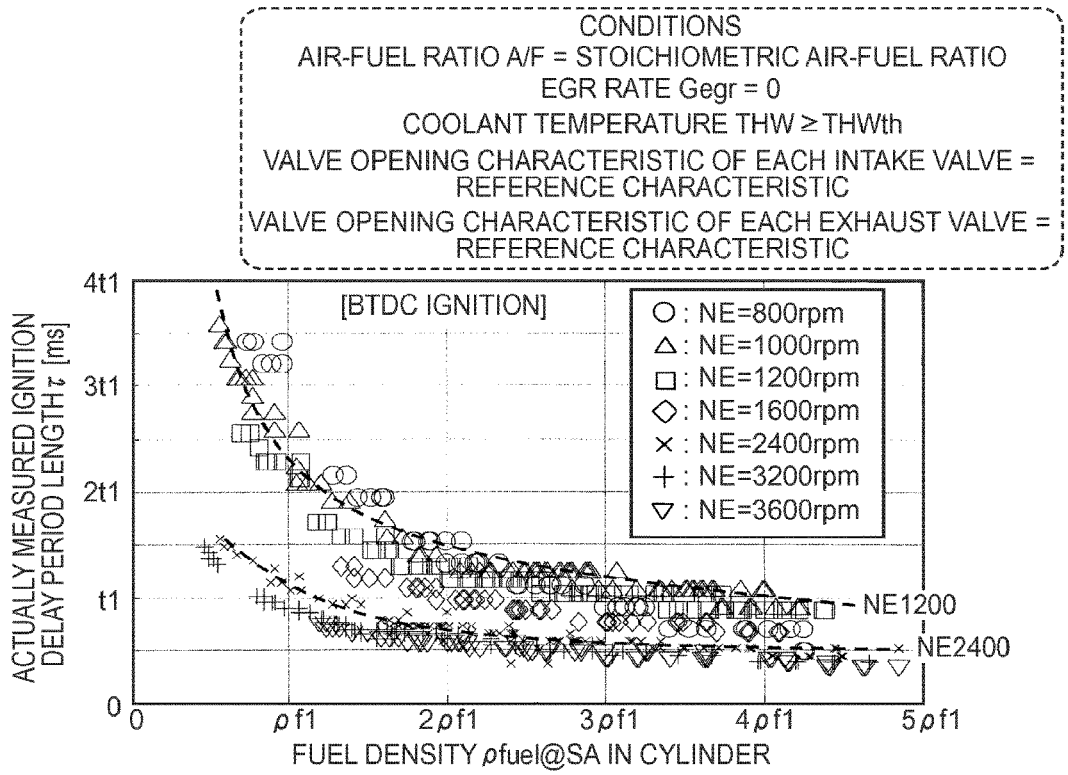
FIG. 9 is a graph that shows the relationship between a fuel density in a cylinder at spark timing and an actually measured ignition delay period length in the case of BTDC ignition.

FIG. 9 is a graph that shows the actually measured results of the relationship between the fuel density ρfuel@SA in the cylinder and the ignition delay period length τ[ms] for various engine rotation speeds NE in the case of BTDC ignition and all the conditions τ1 to τ5 are satisfied.

As is understood from FIG. 9, in the case of BTDC ignition, there is a strong correlation at each engine rotation speed NE between the fuel density ρfuel@SA in the cylinder and the ignition delay period length ρ [ms]. The correlation is expressed in the functional form of the above-described mathematical expression (1). Actually, in FIG. 9, a curve obtained by calculating the relationship between the fuel density ρfuel@SA in the cylinder and the ignition delay period length τ [ms] in the case where the engine rotation speed NE is 1200 [rpm] on the basis of the mathematical expression (1) and a curve obtained by calculating the relationship between the fuel density ρfuel@SA in the cylinder and the ignition delay period length τ [ms] in the case where the engine rotation speed NE is 2400 [rpm] on the basis of the mathematical expression (1) are drawn by dashed lines.

The graph of FIG. 9 will be further described from the physical viewpoint. In the case of BTDC ignition, as the fuel density ρfuel@SA in the cylinder increases, the ignition delay period length τ [ms] shortens. This is presumably because, as the fuel density ρfuel@SA in the cylinder increases, the number of fuel molecules around the ignition plug at the spark timing SA increases and, as a result, a flame kernel rapidly grows after generation of ignition spark. On the other hand, as the engine rotation speed NE increases, the ignition delay period length τ [ms] shortens. This is presumably because, as the engine rotation speed NE increases, the strength of a disturbance of air stream in the cylinder becomes higher and, as a result, a flame kernel rapidly grows after generation of ignition spark.

Figure 10:
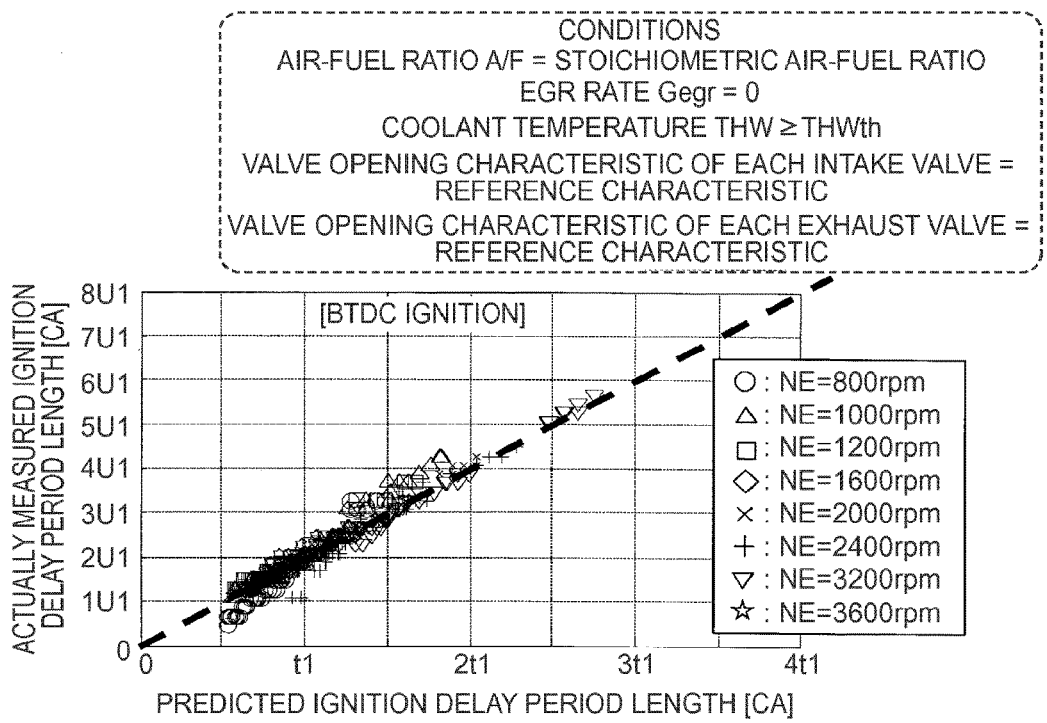
FIG. 10 is a graph that shows the relationship between an ignition delay period length predicted by the embodiment apparatus and an actually measured ignition delay period length in the case of BTDC ignition.

FIG. 10 is a graph that shows the verified results of the relationship between the ignition delay period lengths (predicted ignition delay period lengths) calculated (predicted) by the use of the mathematical expression (1) and the actually measured ignition delay period lengths (actually measured ignition delay period lengths). As is apparent from FIG. 10, the predicted ignition delay period lengths calculated by the use of the mathematical expression (1) accurately coincide with the actually measured ignition delay period lengths. That is, it is understood that the mathematical expression (1) is a mathematical expression (ignition delay period model) suitable for estimating the ignition delay period length τ in the case of BTDC ignition.

Regarding the mathematical expression (2) (in the case of ATDC ignition)

Figure 11:
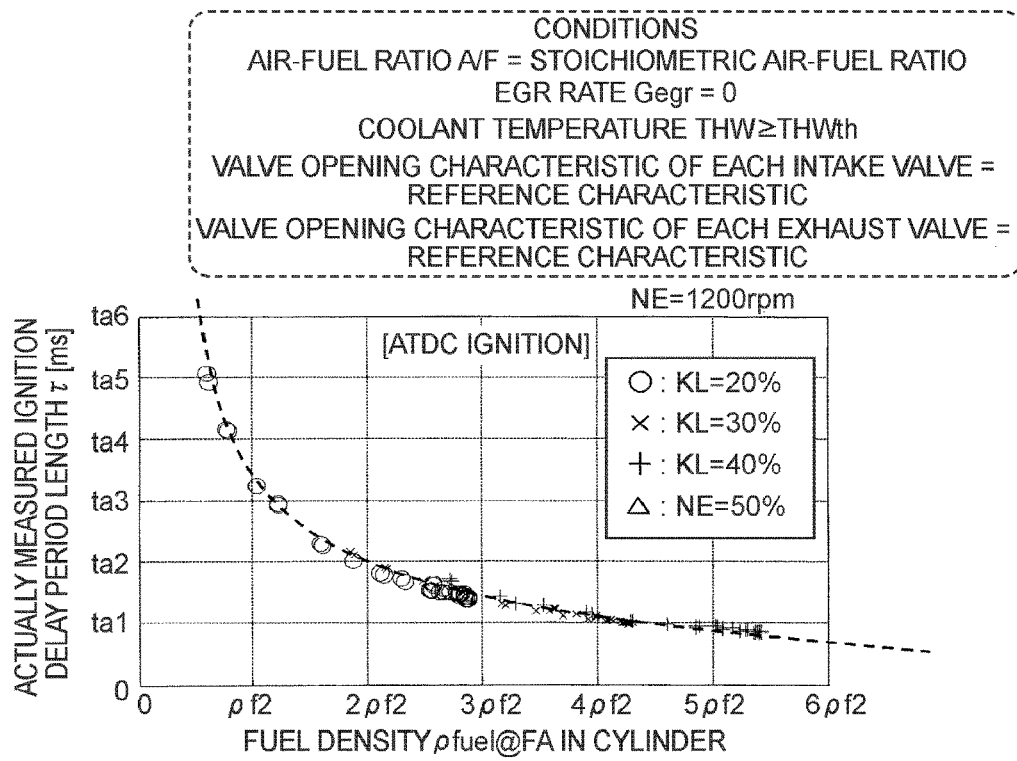
FIG. 11 is a graph that shows the relationship between a fuel density in the cylinder at ignition timing and an actually measured ignition delay period length in the case of ATDC ignition.

FIG. 11 is a graph that shows the actually measured results of the relationship between the fuel density ρfuel@FA in the cylinder and the ignition delay period length τ [ms] for various load factors KL in the case of ATDC ignition and all the conditions τ1 to τ5 are satisfied and when the engine rotation speed NE is 1200 [rpm]. The load factor KL is an air filling fraction, and is calculated by the use of the following mathematical expression where the amount of air that is taken in by one intake stroke of the intended cylinder is Mc [g], the air density is ρ [g/L], the displacement of the engine is Lv [L] and the number of cylinders of the engine is four.

$$KL=\{Mc/(\rho \cdot Lv/4)\} \cdot 100(\%)$$

As is understood from FIG. 11, in the case of ATDC ignition, there is a strong correlation between the fuel density ρfuel@FA in the cylinder and the ignition delay period length τ [ms] irrespective of the load factor KL (that is, irrespective of the load of the engine). The correlation is expressed in the functional form of the above-described mathematical expression (2).

The graph of FIG. 11 will be further described from the physical viewpoint. In the case of ATDC ignition, as the fuel density ρfuel@FA in the cylinder increases, the ignition delay period length τ [ms] shortens. This is presumably because, as in the case of BTDC ignition, as the fuel density ρfuel@FA in the cylinder increases, the number of fuel molecules around the ignition plug in a period just before the ignition timing FA increases and, as a result, a flame kernel rapidly grows. In addition, although not shown in the drawing, as the engine rotation speed NE increases, the ignition delay period length τ [ms] shortens. This is presumably because, as the engine rotation speed NE increases, the strength of a disturbance of air stream in the cylinder becomes higher and, as a result, a flame kernel rapidly grows after generation of ignition spark. Therefore, it is estimated that the engine rotation speed NE is also a parameter that determines the ignition delay period length τ [ms].

Figure 12:
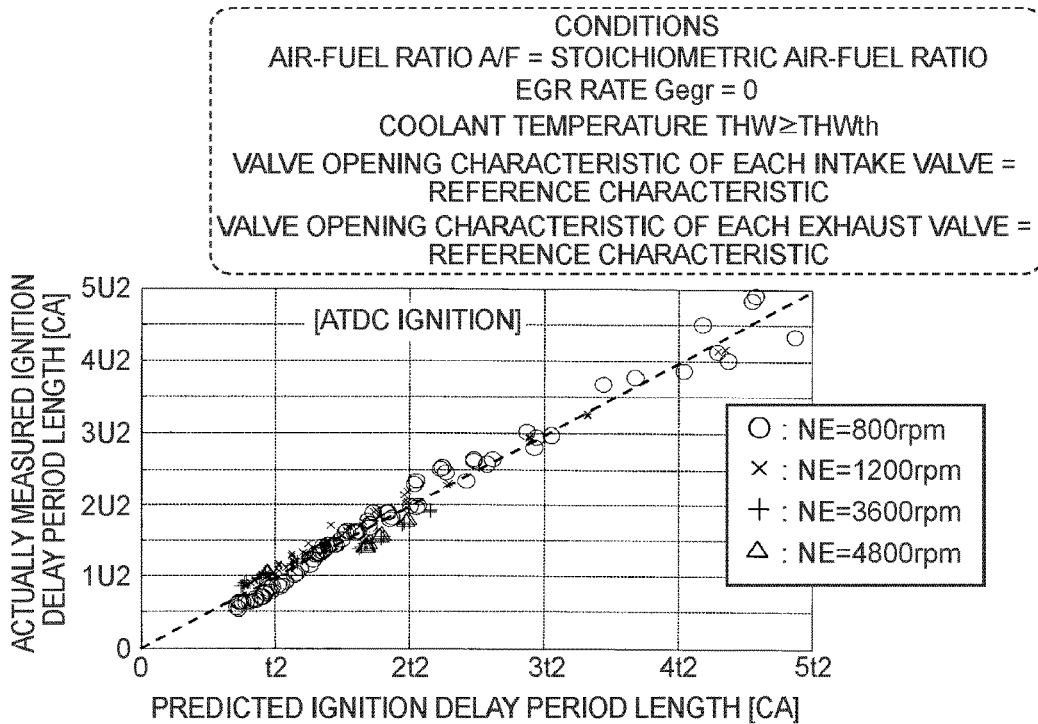
FIG. 12 is a graph that shows the relationship between an ignition delay period length predicted by the embodiment apparatus and an actually measured ignition delay period length in the case of ATDC ignition.

FIG. 12 is a graph that shows the verified results of the relationship between the predicted ignition delay period lengths calculated (predicted) by the use of the mathematical expression (2) and the actually measured ignition delay period lengths. As is apparent from FIG. 12, the predicted ignition delay period lengths calculated by the use of the mathematical expression (2) accurately coincide with the actually measured ignition delay period lengths. That is, it is understood that the mathematical expression (2) is a mathematical expression (ignition delay period model) suitable for estimating the ignition delay period length ti in the case of ATDC ignition.

Reason for selectively using one of the ignition delay period models (the mathematical expression (1) and the mathematical expression (2)) in the case of BTDC ignition and in the case of ATDC ignition A flame kernel produced by ignition spark has grown in the ignition delay period. On the other hand, the combustion chamber volume is momentarily changing in the ignition delay period, so the ρfuel density ρfuel in the cylinder, which strongly correlates with the growth of the flame kernel, is also momentarily changing. Therefore, it is presumably intrinsically suitable to estimate the length of the ignition delay period by the use of the model expression of the ignition delay period. The model expression of the ignition delay period has the fuel density ρfuel in the cylinder, which momentarily changes, as a variable. However, such a model expression of the ignition delay period becomes complex. Therefore, the inventor studied that the fuel density ρfuel at specific timing is employed as a variable of the model expression of the ignition delay period as a typical value of an average value of the fuel density ρfuel in the ignition delay period.

Figure 13:
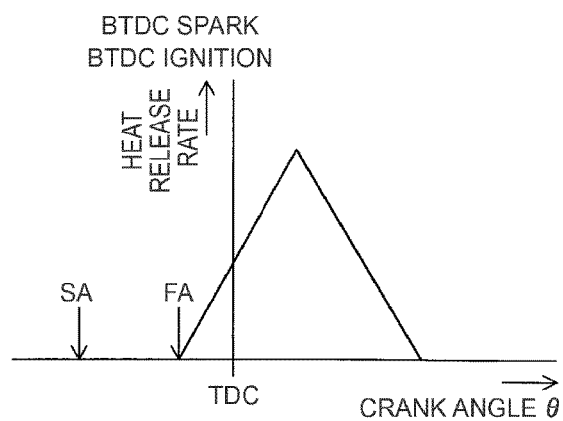
FIG. 13 is a view that conceptually shows a heat release rate waveform in the case of BTDC ignition.

Incidentally, in the case of BTDC ignition, as shown in FIG. 13, not only the ignition timing FA but also the spark timing SA is naturally before the compression top dead center. Thus, in the case of BTDC ignition, the combustion chamber volume reduces (monotonously reduces) during the ignition delay period, and the fuel density ρfuel in the cylinder increases (monotonously increases) accordingly.

Figure 14A:
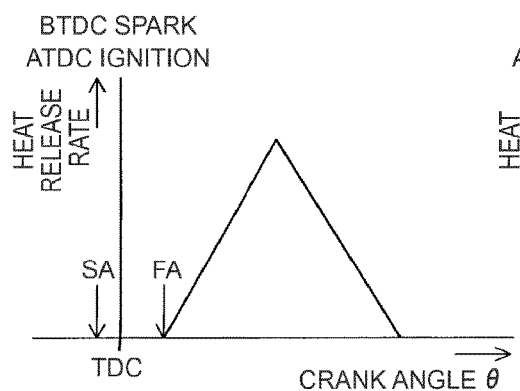
FIG. 14A and FIG. 14B are views that conceptually show heat release rate waveforms in the case of ATDC ignition.
Figure 14B:
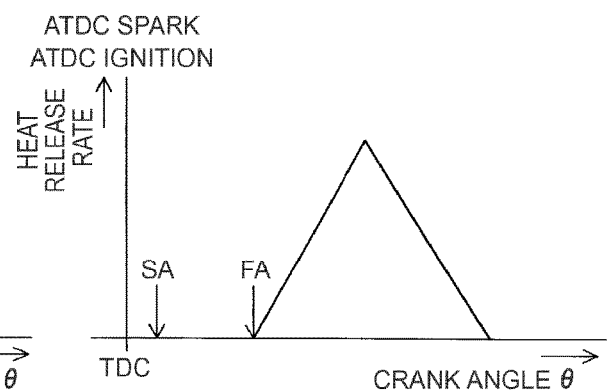

In contrast, in the case of ATDC ignition, as shown in FIG. 14A and FIG. 14B, there are two cases, that is, the case where the spark timing SA is before the compression top dead center (see FIG. 14A) and the case where the spark timing SA is after the compression top dead center (see FIG. 14B).

In the case shown in FIG. 14B, the piston moves toward an expansion bottom dead center after the spark timing SA. That is, in the ignition delay period, the combustion chamber volume increases (monotonously increases), and the fuel density ρfuel in the cylinder reduces (monotonously reduces) accordingly. In the case of FIG. 14A as well, a crank angle difference between the spark timing SA and the compression top dead center is mostly smaller than a crank angle difference between the ignition timing FA and the compression top dead center. In addition, in the case where the crank angle is near the top dead center, a change in combustion chamber volume with respect to a change in crank angle is extremely small, and, after that, when the crank angle distances from near the top dead center, the combustion chamber volume steeply increases with respect to a change in crank angle. Thus, in the case of ATDC ignition, it may be understood that the fuel density ρfuel in the cylinder monotonously reduces during the ignition delay period.

From the above, in the case of BTDC ignition (that is, when the fuel density ρfuel in the cylinder monotonously increases), it is presumable that the fuel density ρfuel@SA at the spark timing is appropriate as a typical value of an average value of the fuel density ρfuel in the ignition delay period. In addition, in the case of ATDC ignition (that is, when the fuel density ρfuel in the cylinder monotonously reduces), it is presumable that the fuel density ρfuel@FA at the ignition timing is appropriate as a typical value of an average value of the fuel density ρfuel in the ignition delay period. The reason why the mathematical expression (1) and the mathematical expression (2) are selectively used is as described above.

2. First Combustion Period Estimation Unit (Outline of First Combustion Period Estimation Unit)

As shown in FIG. 7, the first combustion period is a period from the ignition timing FA to the timing at which the heat release rate dQ/dθ is maximum (that is, maximum heat release rate timing θdQpeak). The first combustion period length a is the length of the first combustion period. The unit of the maximum heat release rate timing θdQpeak is a crank angle [deg] after the compression top dead center. The unit of the first combustion period length a is a crank angle (the width of the crank angle) [CA].

The first combustion period estimation unit 12 estimates the first combustion period length a [CA] by the use of the following mathematical expression (3). However, the first combustion period length a that is estimated by the use of the mathematical expression (3) is a first combustion period length a in the case where the following conditions (a1 and a2) are satisfied. In other words, the mathematical expression (3) holds irrespective of the load factor KL, the EGR rate Gegr, the air-fuel ratio A/F and the coolant temperature THW (engine warm-up state). Grounds for allowing the first combustion period length a to be accurately estimated on the basis of the mathematical expression (3) will be described later. In addition, a method of estimating the first combustion period length a when the following (Condition 1) does not hold, that is, when the valve opening characteristic of each intake valve changes to a characteristic (specific characteristic: intake valve specific characteristic) that differs from the reference characteristic of each intake valve (intake valve reference characteristic) will be described later.

(Condition a1) The valve opening characteristic of each intake valve (the intake valve opening timing IVO, the intake valve closing timing IVC, the intake valve operating angle VCAM, the intake valve phase angle INVT, the maximum value of the intake valve lift IVLift, and the like) is set as the reference characteristic of each intake valve (intake valve reference characteristic). That is, the intake valve opening timing IVO is set to the reference valve opening timing IVOr, the intake valve closing timing IVC is set to the reference valve closing timing IVCr, the intake valve operating angle VCAM is set to the reference valve operating angle VCAMr, the intake valve phase angle INVT is set to the reference phase angle INVTr, and the maximum value of the intake valve lift IVLift is set to the reference maximum value.

(Condition a2) The valve opening characteristic of each exhaust valve (the exhaust valve opening timing EVO, the exhaust valve closing timing EVC, the exhaust valve phase angle EXVT and the maximum value of the exhaust valve lift EVLift, and the like) is set to the reference characteristic of each exhaust valve. That is, the exhaust valve opening timing EVO, the exhaust valve closing timing EVC, the exhaust valve phase angle EXVT and the maximum value of the exhaust valve lift EVLift are respectively set to reference values. Actually, this condition a2 is not indispensable, and the valve opening characteristic of each exhaust valve may be any characteristics.

$$\alpha[CA]=C3 \times V_{@\theta dQpeak}^{\alpha} \times NE^{\beta} \quad (3)$$

In the mathematical expression (3), C3 denotes a constant adapted in advance by experiment, or the like, V@θdQpeak denotes a combustion chamber volume [L] at the maximum heat release rate timing θdQpeak, and α and β each are a constant adapted in advance by experiment, or the like.

Operation of First Combustion Period Estimation Unit

Figure 15:
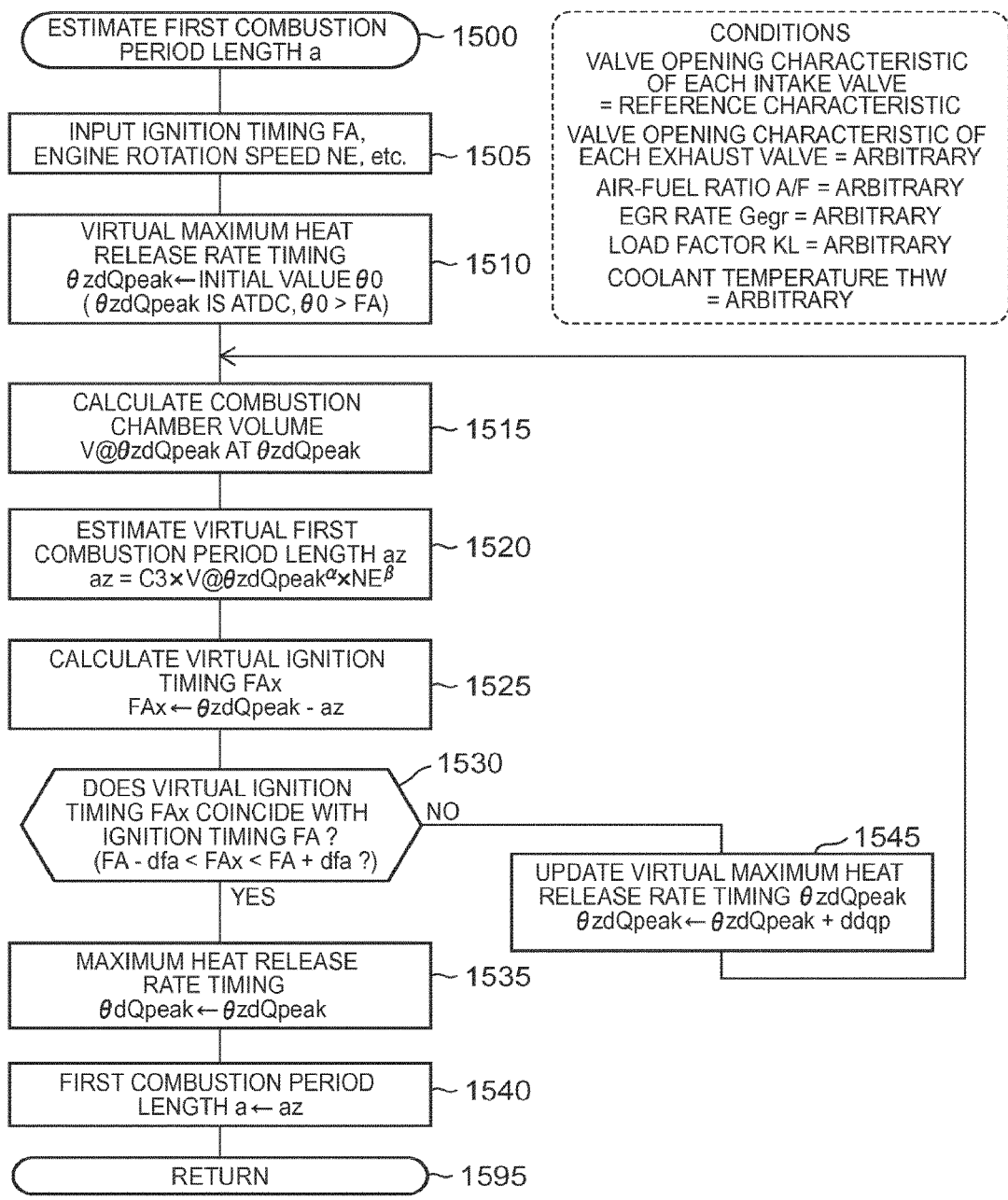
FIG. 15 is a flowchart that shows a routine that is executed by the CPU of the embodiment apparatus.

The CPU estimates the first combustion period length a [CA] in accordance with the routine shown by the flowchart in FIG. 15 in order to implement the function corresponding to the first combustion period estimation unit 12. In the routine shown in FIG. 15, the crank angle is expressed as a crank angle after the compression top dead center (ATDC) (positive value [ATDCdeg] that increases as the crank angle is retarded from the compression top dead center).

The CPU starts the process from step 1500, and sequentially executes the processes of step 1505 to step 1530, which will be described below.

In step 1505, the CPU receives (acquires) various parameters, such as the ignition timing FA and the engine rotation speed NE, estimated above. In step 1510, the CPU sets virtual maximum heat release rate timing θdQpeak to an initial value θ0. The virtual maximum heat release rate timing θdQpeak is maximum heat release rate timing that is virtually (temporarily) set in order to estimate the first combustion period length a. Here, the initial value θ0 is determined in advance to a crank angle larger (on a retard side) by a small positive predetermined crank angle Δθ than the ignition timing FA (FA<θ0=FA+Δθ).

In step 1515, the CPU calculates a combustion chamber volume V@θzdQpeak at the virtual maximum heat release rate timing θdQpeak. As described above, the combustion chamber volume V is uniquely calculated when the crank angle is determined, so the combustion chamber volume V@θzdQpeak is also immediately calculated. In step 1520, the CPU calculates a virtual first combustion period length az [CA] by substituting the combustion chamber volume V@θzdQpeak and the engine rotation speed NE into the same mathematical expression as the mathematical expression (3).

In step 1525, the CPU calculates virtual ignition timing FAx by subtracting the virtual first combustion period length az from the virtual maximum heat release rate timing θzdQpeak (see FIG. 7). In step 1530, the CPU determines whether the virtual ignition timing FAx coincides with the ignition timing FA. Specifically, the CPU determines whether the virtual ignition timing FAx is larger than a crank angle obtained by subtracting a small positive predetermined crank angle dfa from the ignition timing FA and is smaller than a crank angle obtained by adding the crank angle dfa to the ignition timing FA.

When the virtual ignition timing FAx coincides with the ignition timing FA, it is understood that the virtual maximum heat release rate timing θzdQpeak virtually set in order to calculate the virtual first combustion period length az is equal to the actual (true) maximum heat release rate timing θdQpeak. Therefore, when the virtual ignition timing FAx coincides with the ignition timing FA, the CPU makes affirmative determination in step 1530, sequentially executes the processes of step 1535 and step 1540, which will be described later, proceeds to step 1595, and then ends the routine.

In step 1535, the CPU employs the virtual maximum heat release rate timing θzdQpeak as the maximum heat release rate timing θdQpeak. That is, the CPU finally determines the virtual maximum heat release rate timing θzdQpeak at this point in time as the estimated (true) maximum heat release rate timing θdQpeak. In step 1540, the CPU employs the virtual first combustion period length az as the first combustion period length a. That is, the CPU finally determines the virtual first combustion period length az at this point in time as the estimated (true) first combustion period length a.

On the other hand, when the virtual ignition timing FAx does not coincide with the ignition timing FA at the point in time at which the CPU executes the process of step 1530, the CPU makes negative determination in step 1530, proceeds to step 1545, and then increases the virtual maximum heat release rate timing θzdQpeak by a small positive predetermined value ddqp. That is, the virtual maximum heat release rate timing θzdQpea is changed to a crank angle that is retarded by the predetermined value ddqp After that, the CPU proceeds to step 1515.

Such processes are repeated, and, when the virtual ignition timing FAx coincides with the ignition timing FA in a period during which the virtual maximum heat release rate timing θzdQpeak gradually approaches the expansion bottom dead center, the virtual maximum heat release rate timing θzdQpeak at that point in time is employed as the maximum heat release rate timing θdQpeak, and the virtual first combustion period length az at that point in time is employed as the first combustion period length a.

Validity of First Combustion Period Estimation Unit

Next, the point that it is possible to accurately estimate the first combustion period length a on the basis of the above-described mathematical expression (3) will be described. That is, the point that the mathematical expression (3) is an appropriate model as the first combustion period model will be described.

Figure 16:
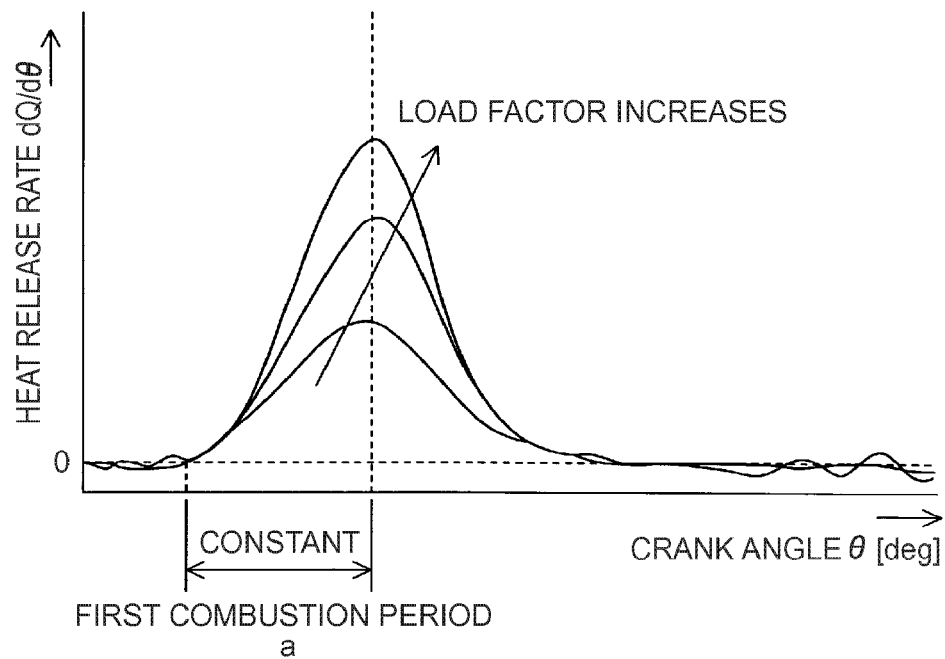
FIG. 16 is a view that conceptually shows heat release rate waveforms for various load factors.
Figure 17:
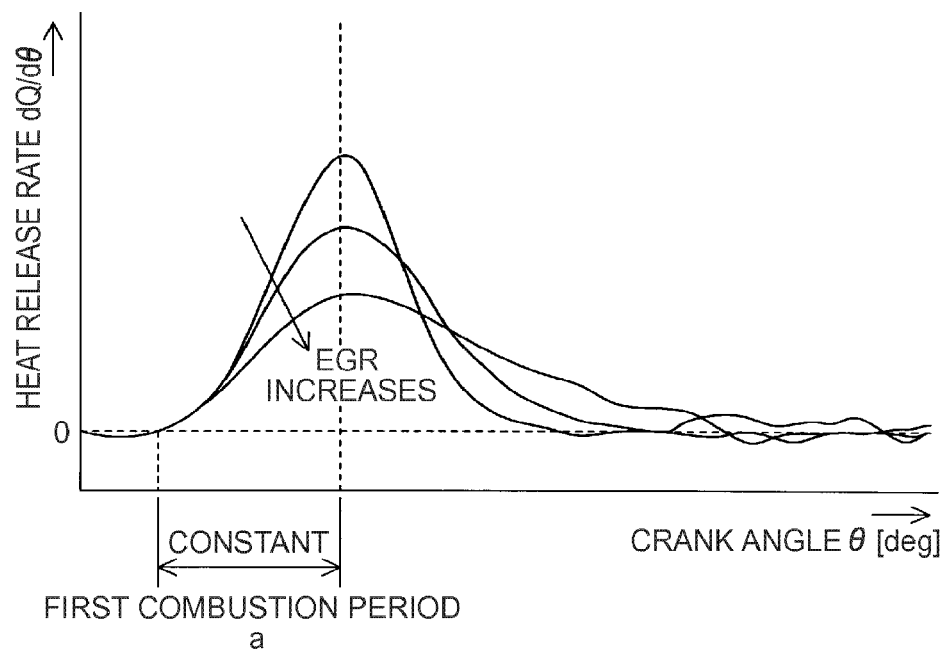
FIG. 17 is a view that conceptually shows heat release rate waveforms for various EGR rates.
Figure 18:
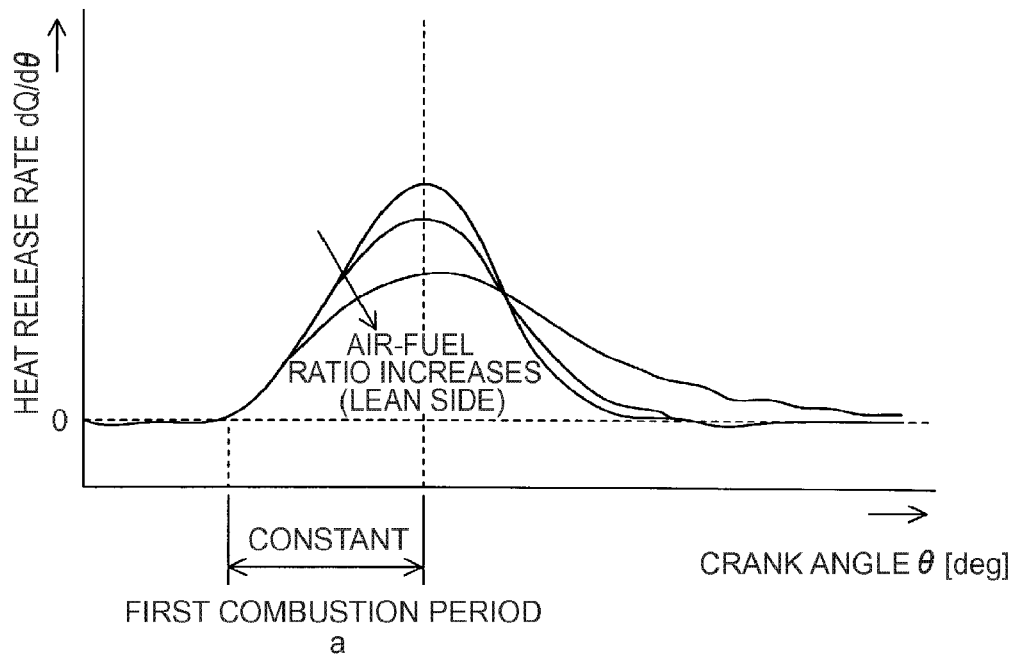
FIG. 18 is a view that conceptually shows heat release rate waveforms for various air-fuel ratios.
Figure 19:
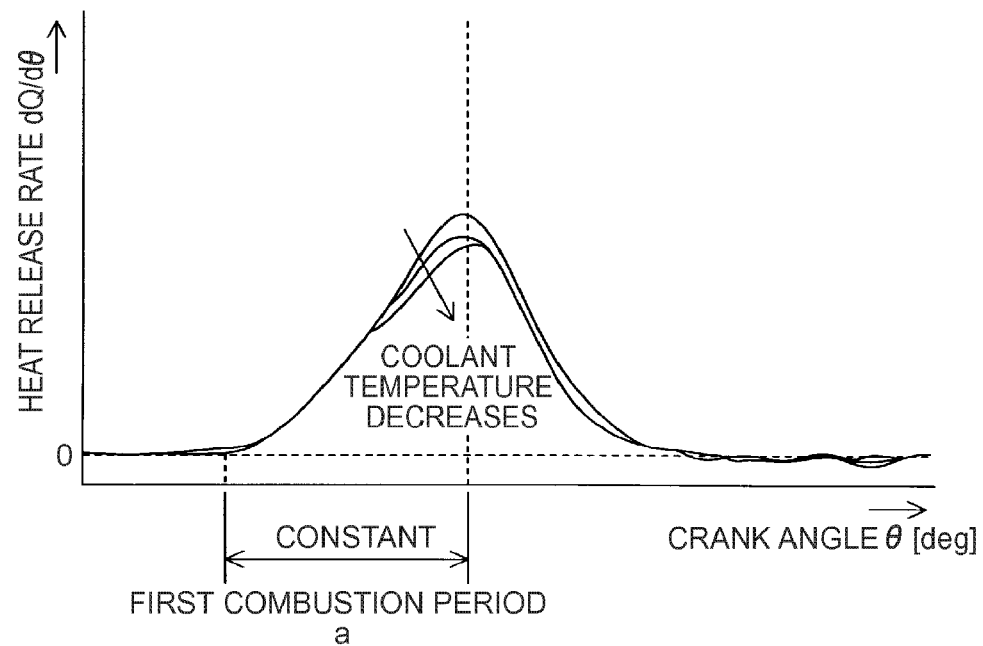
FIG. 19 is a view that conceptually shows heat release rate waveforms for various coolant temperatures.

FIG. 16 is a graph that shows heat release rate waveforms acquired in a plurality of mutually different engine operating states of which only the load factors KL are different from one another among the engine operating state parameters except the spark timing SA and that overlappingly shows the heat release rate waveforms of which the spark timings SA are adjusted such that the maximum heat release rate timings θdQpeak coincide with one another. FIG. 17 is a graph that shows heat release rate waveforms acquired in a plurality of mutually different engine operating states of which only the EGR rates Gegr are different from one another among the engine operating state parameters except the spark timing SA and that overlappingly shows the heat release rate waveforms of which the spark timings SA are adjusted such that the maximum heat release rate timings θdQpeak coincide with one another. FIG. 18 is a graph that shows heat release rate waveforms acquired in a plurality of mutually different engine operating states of which only the air-fuel ratios A/F are different from one another among the engine operating state parameters except the spark timing SA and that overlappingly shows the heat release rate waveforms of which the spark timings SA are adjusted such that the maximum heat release rate timings θdQpeak coincide with one another. FIG. 19 is a graph that shows heat release rate waveforms acquired in a plurality of mutually different engine operating states of which only the coolant temperatures THW are different from one another (that is, operating states of which only the engine warm-up states are different from one another) among the engine operating state parameters except the spark timing SA and that overlappingly shows the heat release rate waveforms of which the spark timings SA are adjusted such that the maximum heat release rate timings θdQpeak coincide with one another.

As is understood from FIG. 16 to FIG. 19, the first combustion period length a is kept constant even when any one of the load factor KL, the EGR rate Gegr, the air-fuel ratio A/F and the coolant temperature THW changes. In other words, it is understood that the first combustion period length a is not dependent on and not influenced by the load factor KL, the EGR rate Gegr, the air-fuel ratio A/F or the coolant temperature THW (that is, the engine warm-up state).

Figure 20:
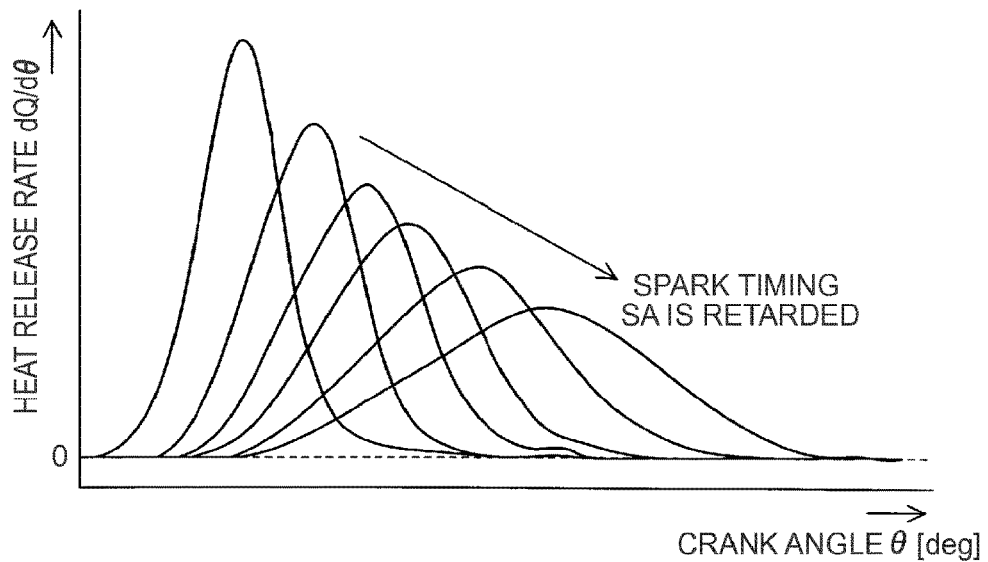
FIG. 20 is a view that conceptually shows heat release rate waveforms for various spark timings.

In contrast, FIG. 20 is a graph that overlappingly shows heat release rate waveforms acquired in a plurality of engine operating states of which only the spark timings SA are different from one another among the engine operating state parameters. It is understood from FIG. 20 that the first combustion period length a extends as the spark timing SA is retarded.

This is presumably because the spark timing SA correlates with the strength of a disturbance in the cylinder in a period from the ignition timing FA to the maximum heat release rate timing θdQpeak (hereinafter, also referred to as the degree of air stream disturbance during the first combustion period). That is, as the spark timing SA is shifted to a more retard side, the ignition timing FA and the maximum heat release rate timing θdQpeak are also shifted to a retard side. As a result, the degree of air stream disturbance during the first combustion period becomes weak, and the combustion chamber volume V@θdQpeak at the maximum heat release rate timing θdQpeak increases. Therefore, it is inferable that a flame spread speed decreases as the spark timing SA is shifted to a more retard side and, as a result, the first combustion period length a extends.

Figure 21:
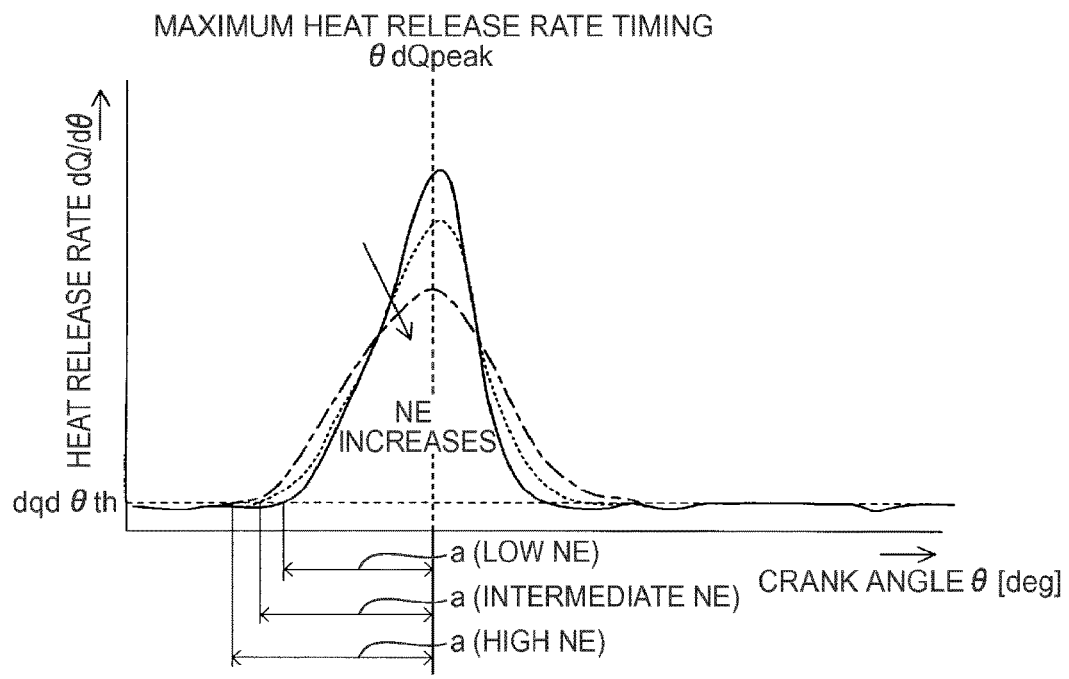
FIG. 21 is a view that conceptually shows heat release rate waveforms for various engine rotation speeds.

FIG. 21 is a graph that shows heat release rate waveforms acquired in a plurality of mutually different engine operating states of which only the engine rotation speeds NE are different from one another among the engine operating state parameters except the spark timing SA and that overlappingly shows the heat release rate waveforms of which the spark timings SA are adjusted such that the maximum heat release rate timings θdQpeak coincide with one another. As is understood from FIG. 21, the first combustion period length a [CA] extends as the engine rotation speed NE increases. For this reason, it is inferable that there is a factor to extend the first combustion period length a [CA] as the engine rotation speed NE increases.

When this factor is studied, it is presumable that the engine rotation speed NE correlates with the degree of air stream disturbance during the first combustion period. Generally, as the engine rotation speed NE increases, the velocity of flow of air flowing from an intake system into the cylinder increases, so the degree of disturbance of air stream formed in the combustion chamber increases. However, the degree (proportion) to which the first combustion period length a [CA] shortens as a result of the degree of disturbance of the air stream is not inversely proportional to the degree (proportion) of an increase in engine rotation speed NE. That is, for example, even when the engine rotation speed NE doubles, the first combustion period length a [CA] does not become half and is longer than a half value. Therefore, it is inferable that the first combustion period length a [CA] extends as the engine rotation speed NE increases and the first combustion period length a [CA] shortens as the engine rotation speed NE decreases.

As a result of the above-described study, the inventor obtained the above-described mathematical expression (3) by employing the engine rotation speed NE and the combustion chamber volume V@θdQpeak at the maximum heat release rate timing θdQpeak as parameters that influence the first combustion period length a (main parameters for estimating the first combustion period length a). The combustion chamber volume V@θdQpeak at the maximum heat release rate timing θdQpeak is a physical quantity that correlates with the spark timing SA.

The coefficients in the above-described mathematical expression (3) will be additionally described. C3 and α in the mathematical expression (3) are identified on the basis of experiment, or the like. β in the mathematical expression (3) is determined so as to increase as a tumble ratio increases. Instead, β may be identified on the basis of experiment, or the like.

Figure 22:
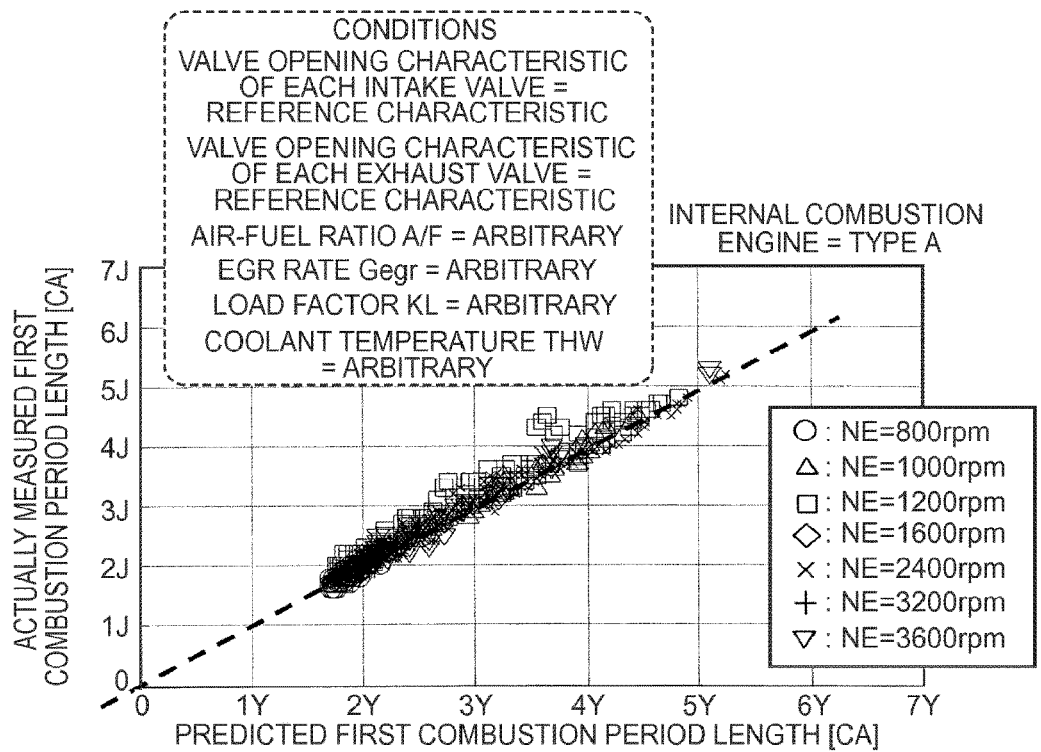
FIG. 22 is a graph that shows the relationship between first combustion period lengths predicted by the embodiment apparatus and actually measured first combustion period lengths in a first-type internal combustion engine.
Figure 23:
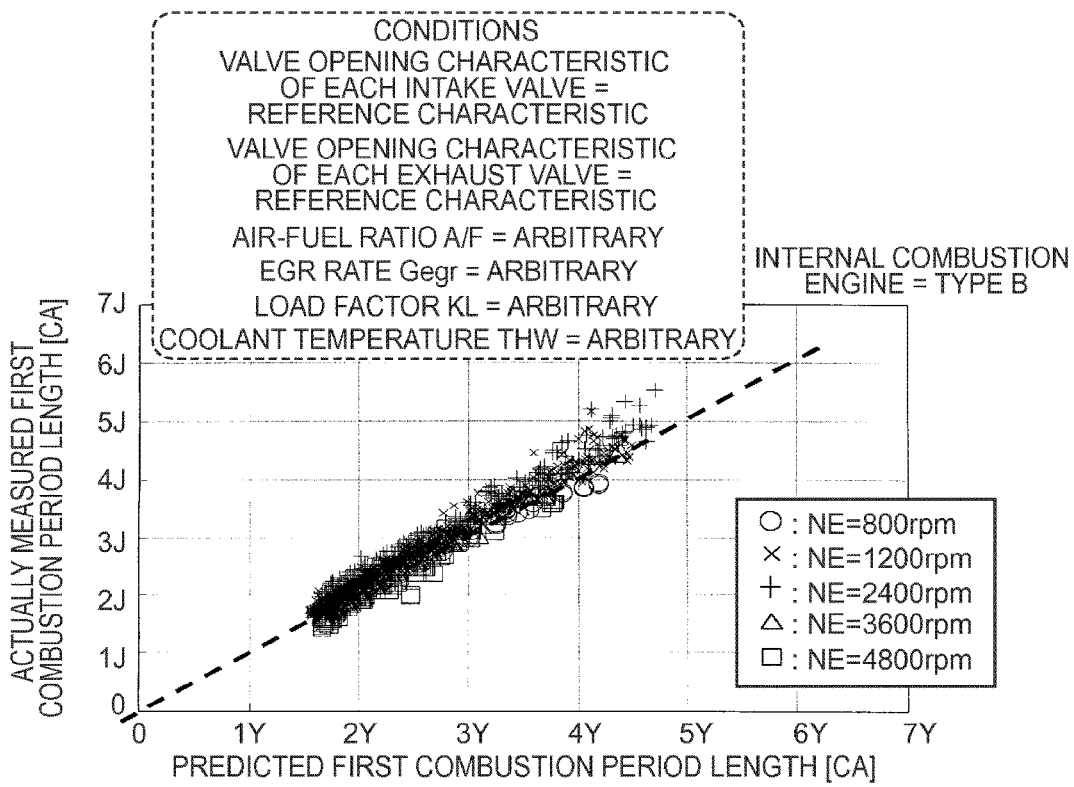
FIG. 23 is a graph that shows the relationship between first combustion period lengths predicted by the embodiment apparatus and actually measured first combustion period lengths in a second-type internal combustion engine.

FIG. 22 and FIG. 23 are graphs that show verified results of the relationships between the first combustion periods (predicted first combustion periods) calculated by the use of the mathematical expression (3) and the actually measured first combustion periods (actually measured first combustion periods) for mutually different internal combustion engines. As is apparent from FIG. 22 and FIG. 23, the predicted first combustion periods calculated by the use of the mathematical expression (3) accurately coincide with the actually measured first combustion periods. That is, it is understood that the mathematical expression (3) is a mathematical expression (first combustion period model) suitable for estimating the first combustion period length a.

3. Heat Release Rate Gradient Estimation Unit (Outline of Heat Release Rate Gradient Estimation Unit)

As shown in FIG. 7, the heat release rate gradient b/a (=G) is the gradient of the heat release rate dQ/dθ in the first combustion period length a (the average value of the rate of increase in heat release rate in the first combustion period). The unit of the heat release rate gradient b/a is $J/CA^2$.

The heat release rate gradient estimation unit 13 estimates the heat release rate gradient b/a by the use of the following mathematical expression (4). However, the heat release rate gradient b/a that is estimated here is the heat release rate gradient b/a in the case where all the following conditions are satisfied. Grounds for allowing the heat release rate gradient b/a to be accurately estimated on the basis of the mathematical expression (4) will be described later.

(Condition G1) The air-fuel ratio A/F of air-fuel mixture that is subjected to combustion is the stoichiometric air-fuel ratio (for example, 14.6).

(Condition G2) The EGR rate Gegr is zero. That is, external EGR is not carried out.

(Condition G3) The coolant temperature THW is higher than or equal to a coolant temperature threshold Tth (for example, 80° C.) that indicates a complete engine warm-up end. The condition G3 is a condition that the engine has been completely warmed up, so the temperature of lubricating oil for the engine may be used in determination as to the condition G3 instead of the coolant temperature THW.

(Condition G4) The valve opening characteristic of each intake valve (the intake valve opening timing IVO, the intake valve closing timing IVC, the intake valve operating angle VCAM, the intake valve phase angle INVT, the maximum value of the intake valve lift IVLift, and the like) is set as the reference characteristic of each intake valve (intake valve reference characteristic). That is, the intake valve opening timing IVO is set to reference valve opening timing IVOr, the intake valve closing timing IVC is set to reference valve closing timing IVCr, the intake valve operating angle VCAM is set to a reference valve operating angle VCAMr, the intake valve phase angle INVT is set to a reference phase angle INVTr, and the maximum value of the intake valve lift IVLift is set to a reference maximum value.

(Condition G5) The valve opening characteristic of each exhaust valve (the exhaust valve opening timing EVO, the exhaust valve closing timing EVC, the exhaust valve phase angle EXVT and the maximum value of the exhaust valve lift EVLift, and the like) is set to the reference characteristic of each exhaust valve. That is, the exhaust valve opening timing EVO, the exhaust valve closing timing EVC, the exhaust valve phase angle EXVT and the maximum value of the exhaust valve lift EVLift are respectively set to reference values.

$$b/a = C4 \times \rho_{fuel@\theta dQpeak} \times NE^\gamma \quad (4)$$

In the mathematical expression (4), C4 and γ denote constants adapted in advance by experiment, or the like, and ρfuel@θdQpeak is a fuel density in the cylinder (in the combustion chamber) at the maximum heat release rate timing θdQpeak (=In-cylinder fuel amount [mol]/Combustion chamber volume [L] at the maximum heat release rate timing θdQpeak) in the case where no combustion occurs.

Operation of Heat Release Rate Gradient Estimation Unit

Figure 24:
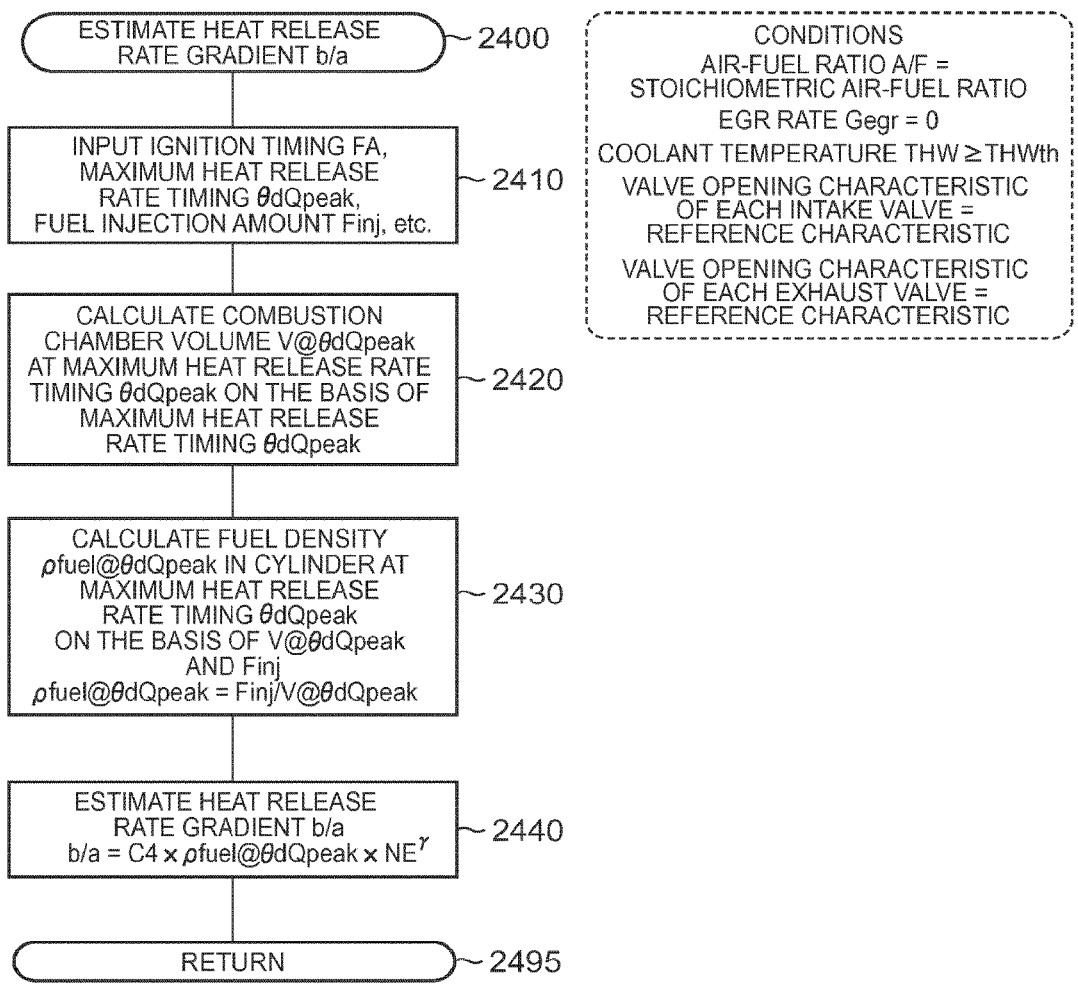
FIG. 24 is a flowchart that shows a routine that is executed by the CPU of the embodiment apparatus.

The CPU estimates the heat release rate gradient b/a in accordance with the routine shown by the flowchart in FIG. 24 in order to implement the function corresponding to the heat release rate gradient estimation unit 13. In the routine shown in FIG. 24, the crank angle is expressed as a crank angle [ATDCdeg] after the compression top dead center (ATDC).

The CPU starts the process from step 2400, sequentially executes the processes of step 2410 to step 2440, which will be described later, proceeds to step 2495, and then ends the routine.

In step 2410, the CPU receives (acquires) various parameters, such as the ignition timing FA, the maximum heat release rate timing θdQpeak and the fuel injection amount Finj, estimated above. In step 2420, the CPU calculates the combustion chamber volume V@θdQpeak at the maximum heat release rate timing θdQpeak. In step 2430, the CPU calculates the fuel density ρfuel@θdQpeak in the cylinder at the maximum heat release rate timing θdQpeak by dividing the fuel injection amount Finj by the combustion chamber volume V@θdQpeak. In step 2440, the CPU calculates the heat release rate gradient b/a by substituting the fuel density ρfuel@θdQpeak in the cylinder into the same mathematical expression as the above-described mathematical expression (4). In this way, the heat release rate gradient b/a is estimated.

Validity of Heat Release Rate Gradient Estimation Unit

Next, the point that it is possible to accurately estimate the heat release rate gradient b/a on the basis of the above-described mathematical expression (4) will be described. That is, the point that the mathematical expression (4) is an appropriate model as the heat release rate gradient model.

FIG. 25A to FIG. 25D are graphs, each of which shows heat release rate waveforms acquired in a plurality of mutually different engine operating states of which only the load factors KL are different from one another among engine operating state parameters except the spark timing SA and that overlappingly shows the heat release rate waveforms of which the spark timings SA are adjusted such that maximum heat release rate timings θdQpeak coincide with one another. The spark timing SA is shifted to a retard side in order of FIG. 25A to FIG. 25D. In FIG. 25A to FIG. 25D, the load factor KL increases in order of KL1, KL2 and KL3.

Figure 26A:
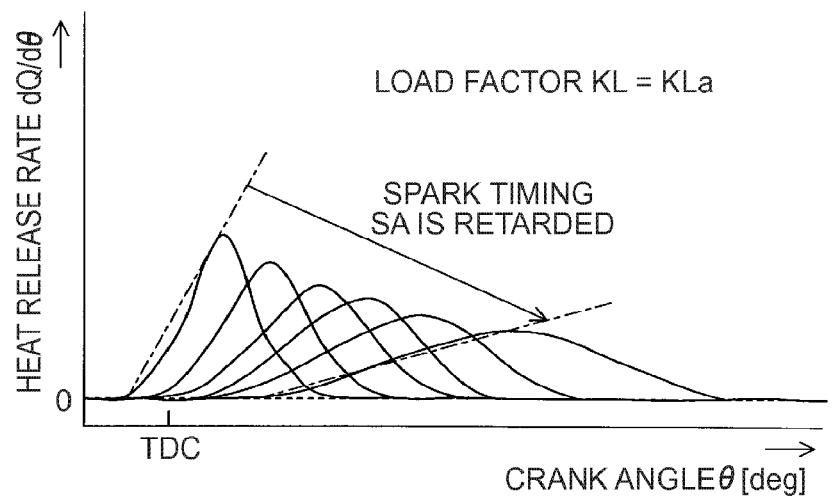
FIG. 26A and FIG. 26B are graphs that show heat release rate waveforms in the case where the spark timing is changed.
Figure 26B:
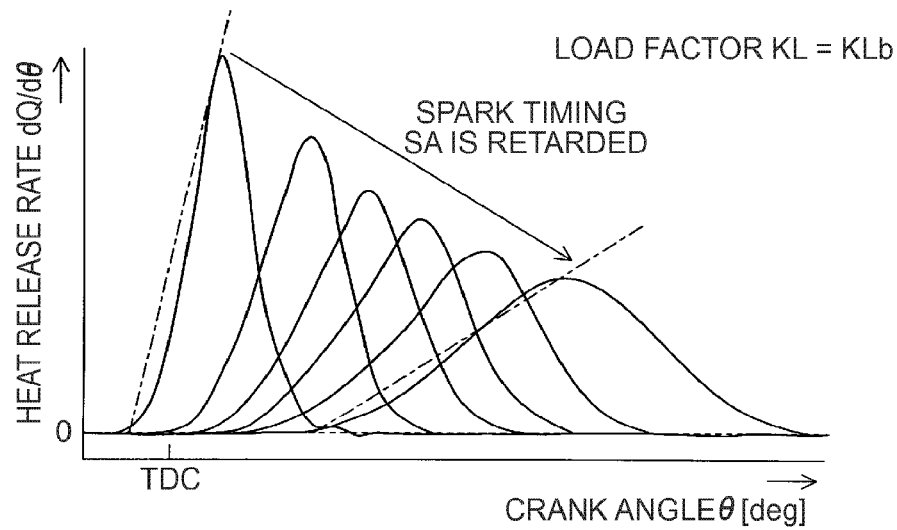
Figure 27A:
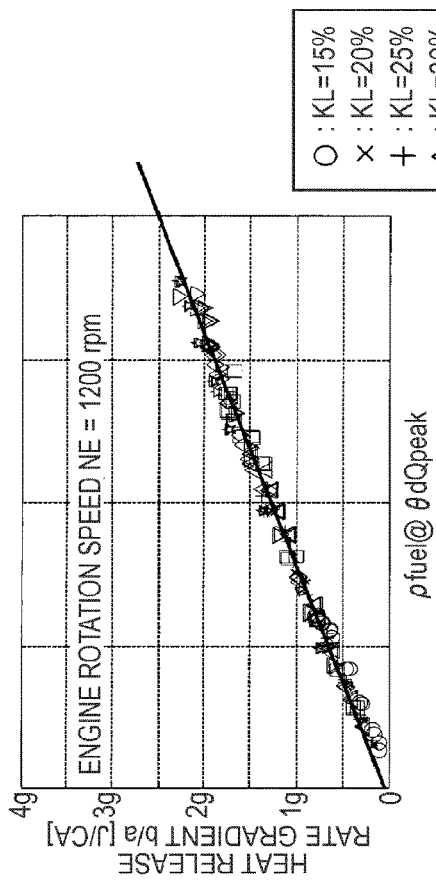
FIG. 27A to FIG. 27D are graphs that respectively show the relationships between a fuel density in the cylinder at maximum heat release rate timing and a heat release rate gradient at various engine rotation speeds.
Figure 27B:
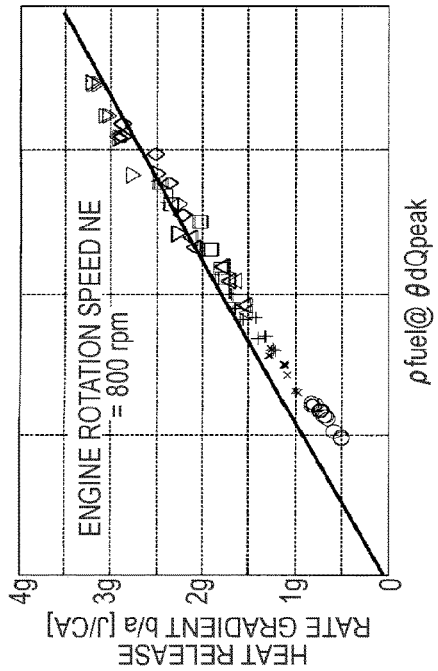
Figure 27C:
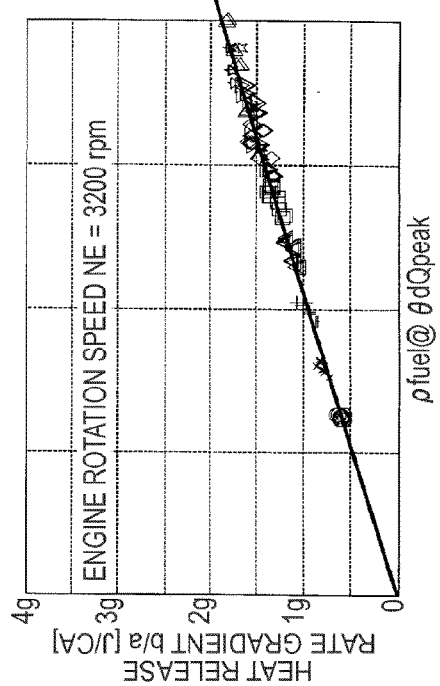
Figure 27D:
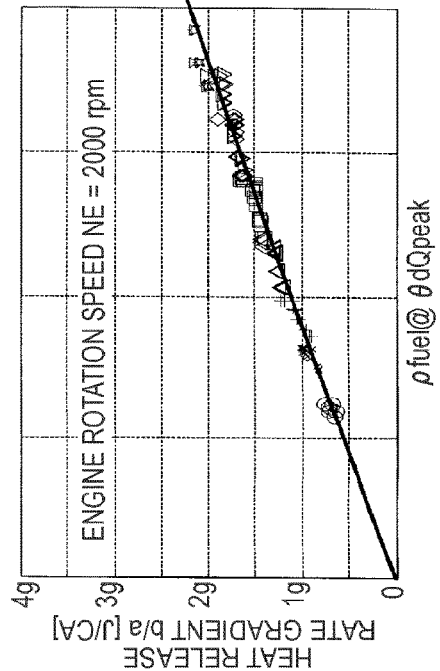

FIG. 26A and FIG. 26B each are a graph that shows heat release rate waveforms acquired in a plurality of engine operating states of which only the spark timings SA are different from one another.

As is understood from FIG. 25A to FIG. 25D and FIG. 26A and FIG. 26B, the heat release rate gradient b/a increases as the load factor KL increases, and increases as the spark timing SA is advanced.

The reason why the heat release rate gradient b/a increases as the load factor KL increases is inferable because the fuel injection amount Finj increases as the load factor KL increases, the fuel density in the cylinder in the first combustion period increases accordingly and, as a result, the combustion speed of air-fuel mixture (flame spread speed) increases.

The reason why the heat release rate gradient b/a increases as the spark timing SA is advanced is inferable because, as in the case of the load factor KL, the fuel density in the cylinder in the first combustion period increases as the spark timing SA is advanced and, as a result, the combustion speed of air-fuel mixture (flame spread speed) increases. That is, when the piston is positioned near the compression top dead center, a change in combustion chamber volume resulting from a change in crank angle is small; however, in expansion stroke (particularly, when the crank angle becomes larger than a crank angle near 10[deg] after the compression top dead center), the combustion chamber volume rapidly increases, so it is inferable that the fuel density in cylinder in the first combustion period decreases and, as a result, the combustion speed of air-fuel mixture (flame spread speed) decreases.

The inventor investigated the relationship between the heat release rate gradient b/a and the fuel density $\rho fuel@\theta dQpeak$ in the cylinder at the maximum heat release rate timing $\theta dQpeak$ for each of various load factors KL and each of various engine rotation speeds NE by experiment. The fuel density $\rho fuel@\theta dQpeak$ in the cylinder at the maximum heat release rate timing $\theta dQpeak$ is a typical value of the fuel density in the cylinder in the first combustion period. The results are shown in FIG. 27A to FIG. 27D.

It is understood from FIG. 27A to FIG. 27D that, when the engine rotation speed NE is constant, the fuel density $\rho fuel@\theta dQpeak$ in the cylinder and the heat release rate gradient b/a have substantially the proportional relationship even when the load factors KL (therefore, the spark timings SA) are different. Therefore, it is understood that the heat release rate gradient calculated by the use of the mathematical expression (4) accurately coincides with the actually measured heat release rate gradient. That is, it is understood that the mathematical expression (4) is a mathematical expression (heat release rate gradient model) suitable for estimating the heat release rate gradient b/a.

4. Heat Release Amount Estimation Unit (Outline of Heat Release Amount Estimation Unit)

As shown in FIG. 7, the total heat release amount Qa11 is the sum of the heat release amount Q1 in the first combustion period and the heat release amount Q2 in a second combustion period. That is, the total heat release amount Qa11 is the total amount of heat generated through one combustion. The unit of these heat release amounts is J. The second combustion period is a period from the maximum heat release rate timing $\theta dQpeak$ to combustion end timing EA at which combustion ends.

The heat release amount estimation unit 14 estimates the heat release rate $dQ/d\theta_{@\theta dQpeak}$ (=b) at the maximum heat release rate timing $\theta dQpeak$, the total heat release amount Qa11, the heat release amount Q1 in the first combustion period, the heat release amount Q2 in the second combustion period, and a second combustion period length c by the use of the following mathematical expression (5) to the mathematical expression (9). The estimated first combustion period length a and heat release rate gradient b/a are applied to the mathematical expression (5). K in the mathematical expression (7) denotes a combustion efficiency. The combustion efficiency K is obtained as follows. The relationship between the combustion efficiency K and a combination of the load factor KL, the engine rotation speed NE and the coolant temperature THW is measured by experiment in advance, a lookup table MapK(KL, NE, THW) that defines the relationship is created on the basis of the measured data, and then the actual load factor KL, engine rotation speed NE and coolant temperature THW are applied to the table MapK(KL, NE, THW). Finj is an actual fuel injection amount as described above. The mathematical expression (6) and the mathematical expression (9) are easily derived from a mathematical expression for obtaining the area of the triangle shown in FIG. 7.

$$b = a \times (b/a) \quad (5)$$

$$Q1 = (1/2) \times a \times b \quad (6)$$

$$Qa11 = Finj \times K \quad (7)$$

$$K = MapK(KL, NE, THW) \quad (7)$$

$$Q2 = Qa11 - Q1 \quad (8)$$

$$c = 2 \times Q2/b \quad (9)$$

Operation of Heat Release Amount Estimation Unit

Figure 28:
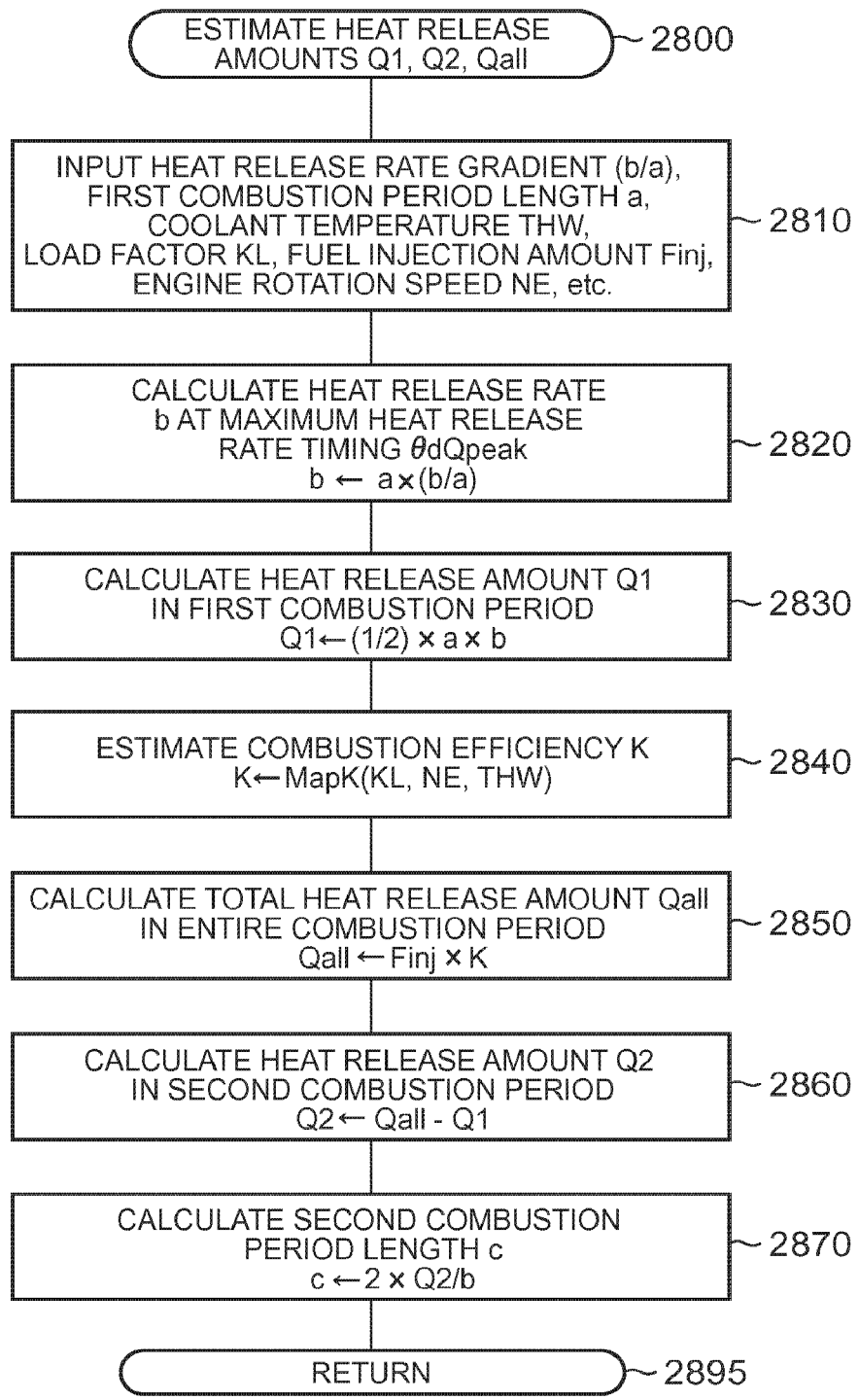
FIG. 28 is a flowchart that shows a routine that is executed by the CPU of the embodiment apparatus.

The CPU estimates the total heat release amount Qa11, the second combustion period, and the like, in accordance with the routine shown by the flowchart in FIG. 28 in order to implement the function corresponding to the heat release amount estimation unit 14. That is, the CPU starts the process from step 2800, sequentially executes the processes of step 2810 to step 2870, which will be described below, proceeds to step 2895, and then ends the routine.

In step 2810, the CPU receives (acquires) the heat release rate gradient b/a and first combustion period length a, estimated above, and various parameters, such as the coolant temperature THW, the load factor KL, the fuel injection amount Finj and the engine rotation speed NE. In step 2820, the CPU calculates the heat release rate b at the maximum heat release rate timing $\theta dQpeak$ by the use of the mathematical expression (5). In step 2830, the CPU calculates the heat release amount Q1 in the first combustion period by the use of the mathematical expression (6). In step 2840, the CPU obtains the combustion efficiency K by applying the actual load factor KL, engine rotation speed NE and coolant temperature THW to the lookup table MapK(KL, NE, THW). In step 2850, the CPU calculates the total heat release amount Qa11 by the use of the above-described mathematical expression (7). In step 2860, the CPU calculates the heat release amount Q2 in the second combustion period by the use of the mathematical expression (8). In step 2870, the CPU calculates the second combustion period length c by the use of the above-described mathematical expression (9).

As described above, the embodiment apparatus 10 is able to estimate the heat release rate waveform QW with the use of the embodiment method.

Estimation of First Combustion Period When Valve Opening Characteristic of Intake Valve Has Changed Incidentally, the condition a1 that is one of the preconditions for the above-described mathematical expression (3) is the condition that holds when the valve opening characteristic of each intake valve is set to the reference characteristic of each intake valve. In other words, when the condition a1 does not hold (that is, when the intake valve opening characteristic differs from the intake valve reference characteristic), the values C3, $\alpha$ and $\beta$ in the above-described mathematical expression (3) need to be determined again. As a result, enormous amounts of time and effort are required in order to estimate the first combustion period length a for each of various valve opening characteristics of each intake valve.

Figure 1:
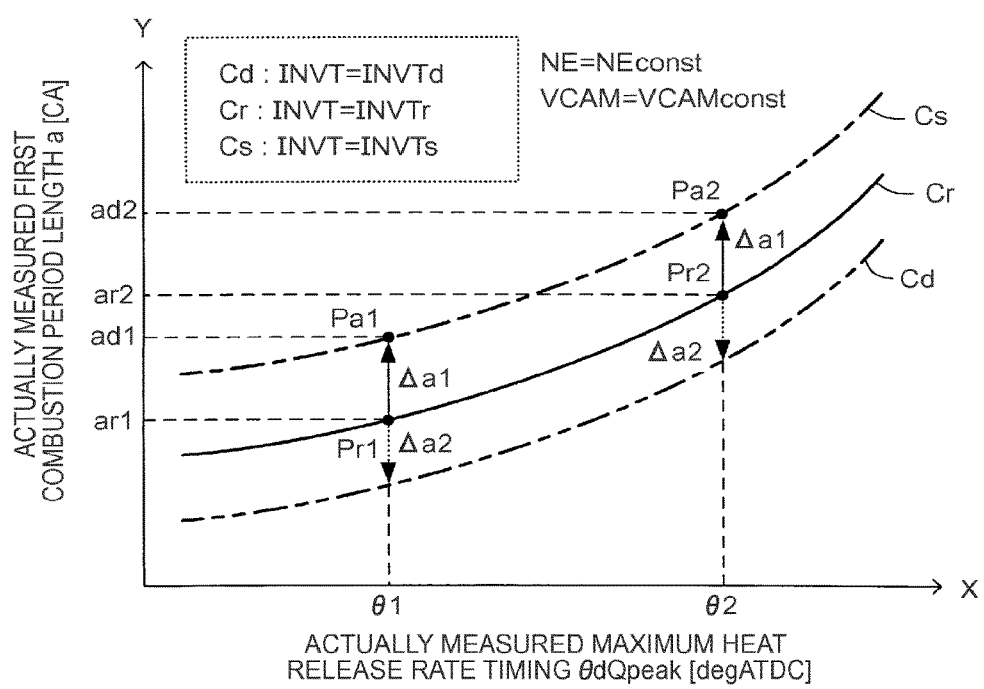
FIG. 1 is a graph that shows the relationship between maximum heat release rate timing and a first combustion period length for each of various intake valve phase angles.
Figure 2A:
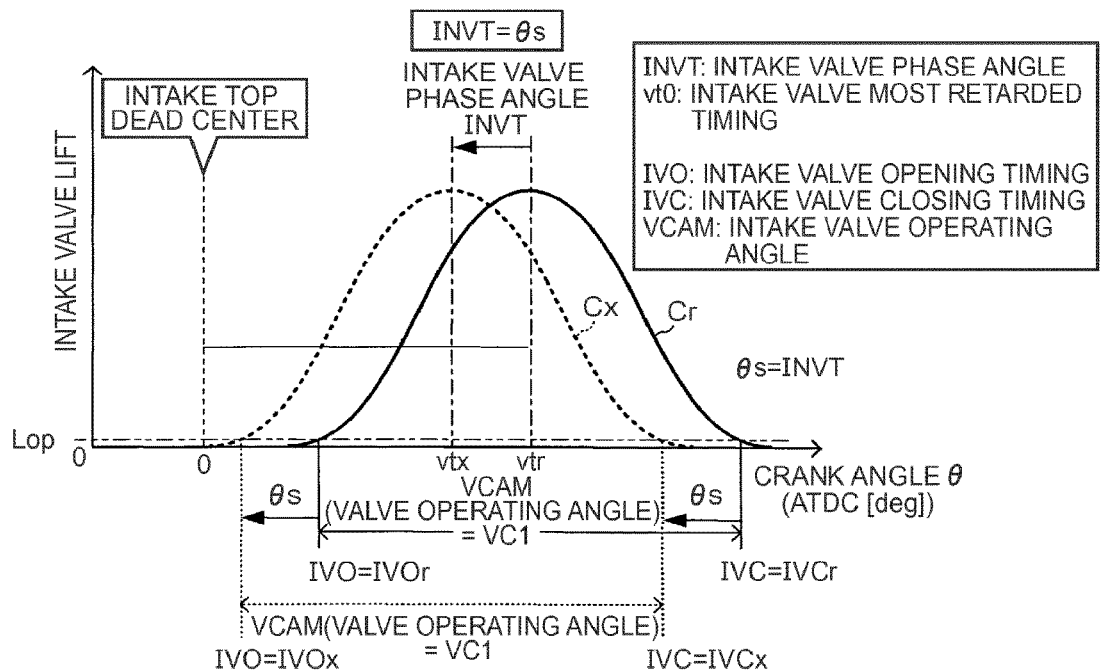
FIG. 2A and FIG. 2B are views for illustrating parameters that define the valve opening characteristic of an intake valve.
Figure 2B:
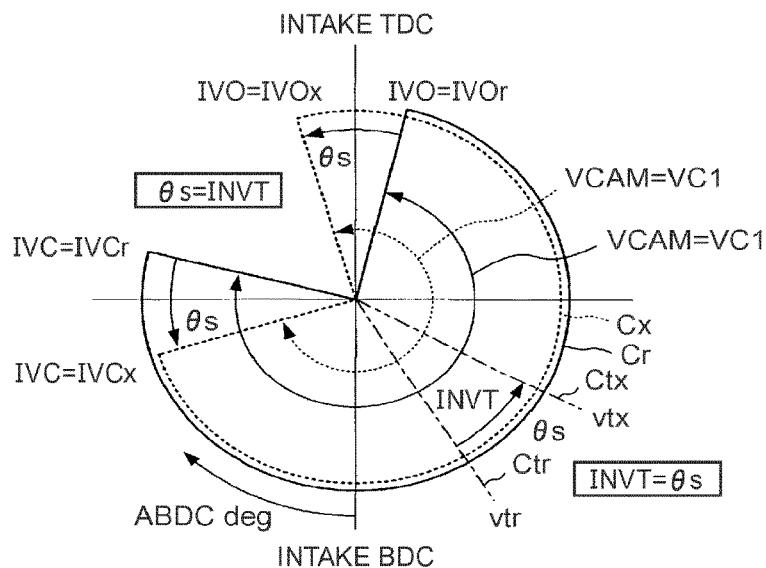

In contrast, as described with reference to FIG. 1 and FIG. 2, the inventor obtained the following findings 1.

(Findings 1) The relationship (that is, the reference relationship) between the maximum heat release rate timing $\theta dQpeak$ and the first combustion period length aref in the case where the engine rotation speed NE is a selected speed NE0, the intake valve operating angle VCAM is a selected operating angle VCAM0 and the intake valve phase angle INVT is a reference phase angle INVTr is expressed by the function aref=f($\theta dQpeak$). At this time, when it is assumed that the first combustion period length as ($\theta$1) at the time when the engine rotation speed NE is the selected speed NE0, the intake valve operating angle VCAM is the selected operating angle VCAM0, the intake valve phase angle INVT is the predetermined phase angle INVTs and the maximum heat release rate timing θdQpeak is a selected value θ1 is ad1, the first combustion period length as(θ2) at the time when the engine rotation speed NE is the selected speed NE0, the intake valve operating angle VCAM is the selected operating angle VCAM0, the intake valve phase angle INVT is the predetermined phase angle INVTs and the maximum heat release rate timing θdQpeak is a selected value θ2 is allowed to be obtained by the use of the following mathematical expression (1B).

$$as(\theta 2)=f(\theta 2)+\Delta a1=f(\theta 2)+(ad1-ar1)=f(\theta 2)-(ar1-ad1)=f(\theta 2)+\{ad1-f(\theta 1)\} \quad (1B)$$

Figure 29:
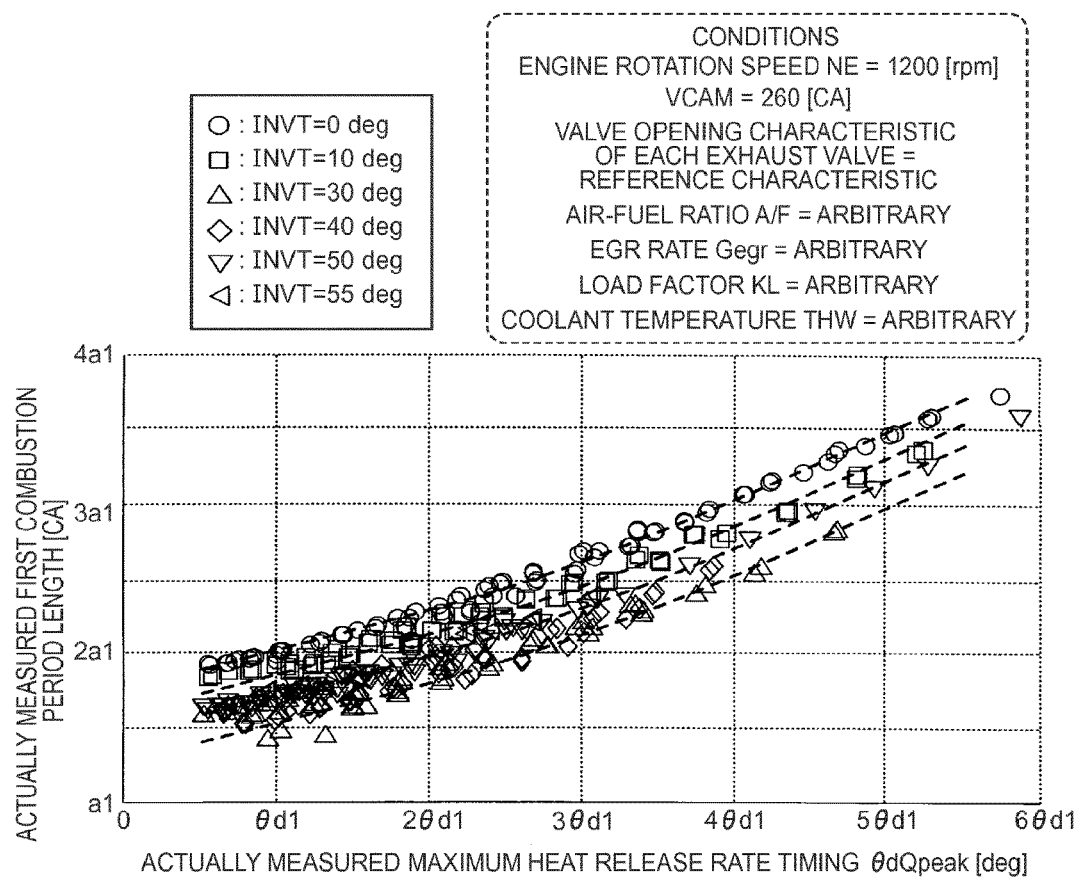
FIG. 29 is a graph that shows the relationship between actually measured maximum heat release rate timings and actually measured first combustion period lengths for various intake valve phase angles in the case where the engine rotation speed and the intake valve operating angle are kept constant.

Hereinafter, the validity of the above findings 1 will be described. FIG. 29 is a graph in which the relationship between the actually measured maximum heat release rate timings θdQpeak and the actually measured first combustion period lengths a is plotted in experiment in which, in the case where the engine rotation speed NE is a constant speed (=1200 [rpm]), the intake valve operating angle VCAM is fixed to a constant operating angle (=260[CA]) and the intake valve phase angle INVT is changed to various values.

It is understood from the graph shown in FIG. 29 that curves (dashed lines) that define the relationships between the maximum heat release rate timing θdQpeak and the first combustion period length a strongly correlate with the intake valve phase angle INVT and are translated in the direction in which the first combustion period length a increases or reduces (sheet vertical direction), that is, Y-axis direction) as the intake valve phase angle INVT changes.

Figure 30A:
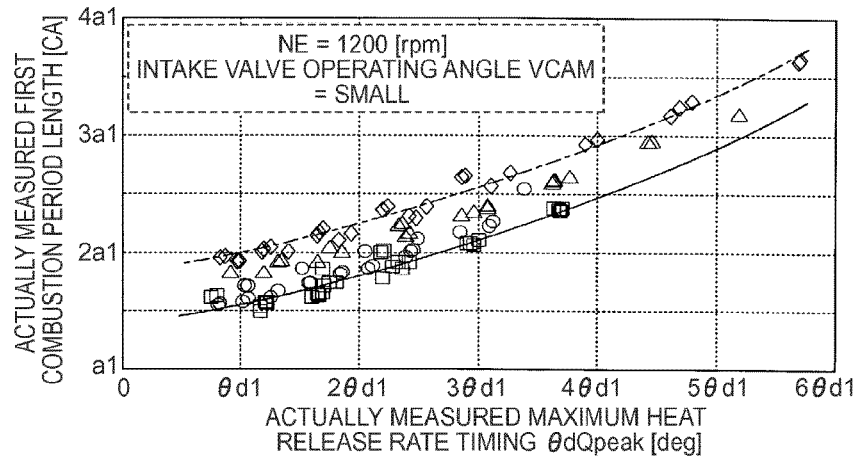
FIG. 30A to FIG. 30C each are a graph that shows the relationship between actually measured maximum heat release rate timings and actually measured first combustion period lengths for each of various intake valve phase angles in the case where the engine rotation speed and the intake valve operating angle are kept constant.
Figure 30B:
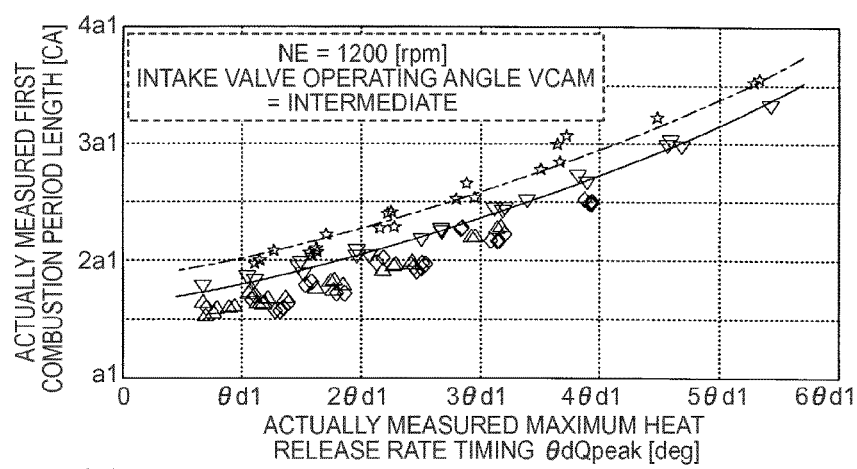
Figure 30C:
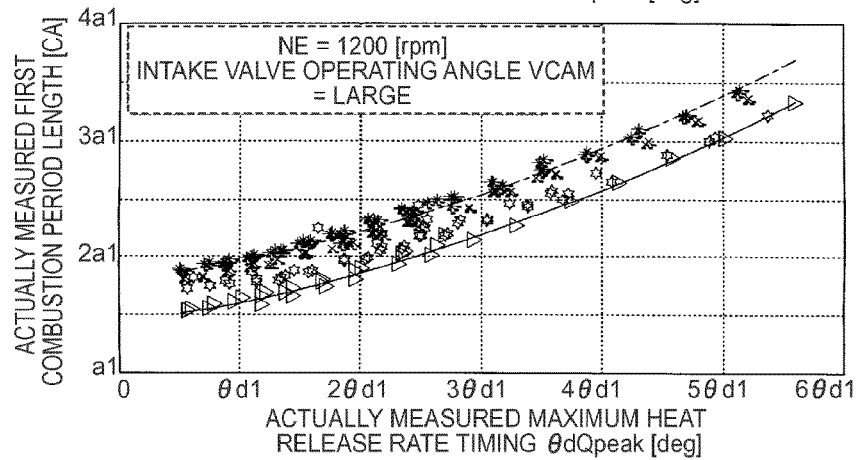

Each of the graphs shown in FIG. 30A to FIG. 30C is a graph in which the relationship between the actually measured maximum heat release rate timings θdQpeak and the actually measured first combustion period lengths a is plotted in experiment in which, when the engine rotation speed NE is 1200 [rpm], the intake valve operating angle VCAM is fixed to any one of various values, and the intake valve closing timing IVC is changed to various values by changing the intake valve phase angle INVT to various values.

Legends in the graphs shown in FIG. 30A to FIG. 30C are shown in TABLE 1.

TABLE 1

| ○: IVC = −50 deg | ▷: IVC = 20 deg |
|---|---|
| □ : IVC = −35 deg | ☆: IVC = 25 deg |
| Δ: IVC = −20 deg | ✿ IVC = 30 deg |
| ◇ : IVC = −5 deg | ×: IVC = 40 deg |
| ∇: IVC = 10 deg | ✳: IVC = 50 deg |
| ◁ IVC = 15 deg | +: IVC = 60 deg |

The graphs shown in FIG. 30A to FIG. 30C indicate that, when the intake valve operating angle VCAM is fixed to any one of various values in the case where the engine rotation speed NE is 1200 [rpm], the relationship is translated in the direction in which the first combustion period length a increases or reduces as the intake valve phase angle INVT changes.

Figure 31A:
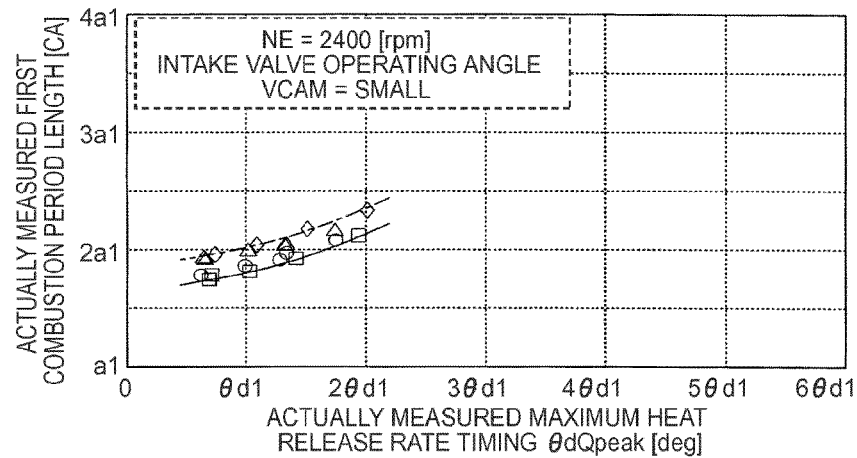
FIG. 31A to FIG. 31C each are a graph that shows the relationship between actually measured maximum heat release rate timings and actually measured first combustion period lengths for each of various intake valve phase angles in the case where the engine rotation speed and the intake valve operating angle are kept constant.
Figure 31B:
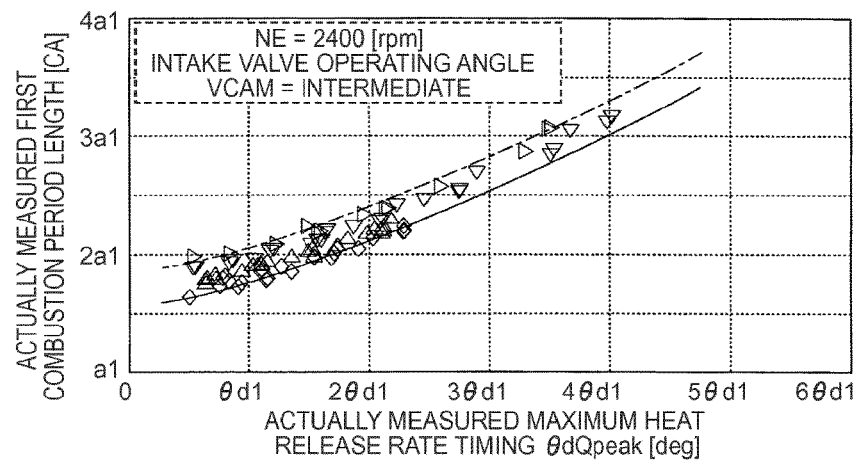
Figure 31C:
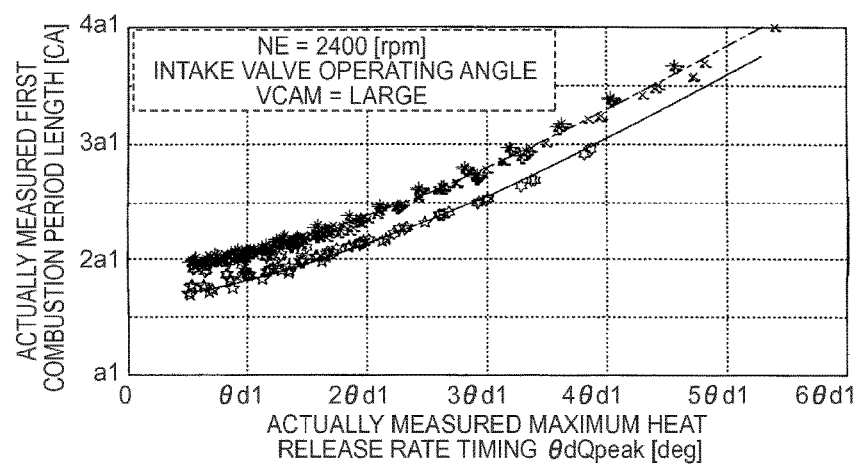

Similarly, each of the graphs shown in FIG. 31A to FIG. 31C is a graph in which the relationship between the actually measured maximum heat release rate timings θdQpeak and the actually measured first combustion period lengths a is plotted in experiment in which the engine rotation speed NE is 2400 [rpm], the intake valve operating angle VCAM is fixed to any one of various values, and the intake valve closing timing IVC is changed to various values by changing the intake valve phase angle INVT to various values. Legends in the graphs shown in FIG. 31A to FIG. 31C are the same as the legends shown in TABLE 1.

The graphs shown in FIG. 31A to FIG. 31C indicate that, when the intake valve operating angle VCAM is fixed to any one of various values in the case where the engine rotation speed NE is 2400 [rpm], the relationship is translated in the direction in which the first combustion period length a increases or reduces as the intake valve phase angle INVT changes. It is understood from the graphs shown in FIG. 30A to FIG. 30C and the graphs shown in FIG. 31A to FIG. 31C that, even when the engine rotation speed NE is different, as long as the engine rotation speed NE is kept constant and the intake valve operating angle VCAM is kept constant, the relationship is translated in the direction in which the first combustion period length a increases or reduces as the intake valve phase angle INVT changes.

As described above, the validity of the findings 1 is verified by the graphs shown in FIG. 30A to FIG. 30C and FIG. 31A to FIG. 31C.

Figure 3:
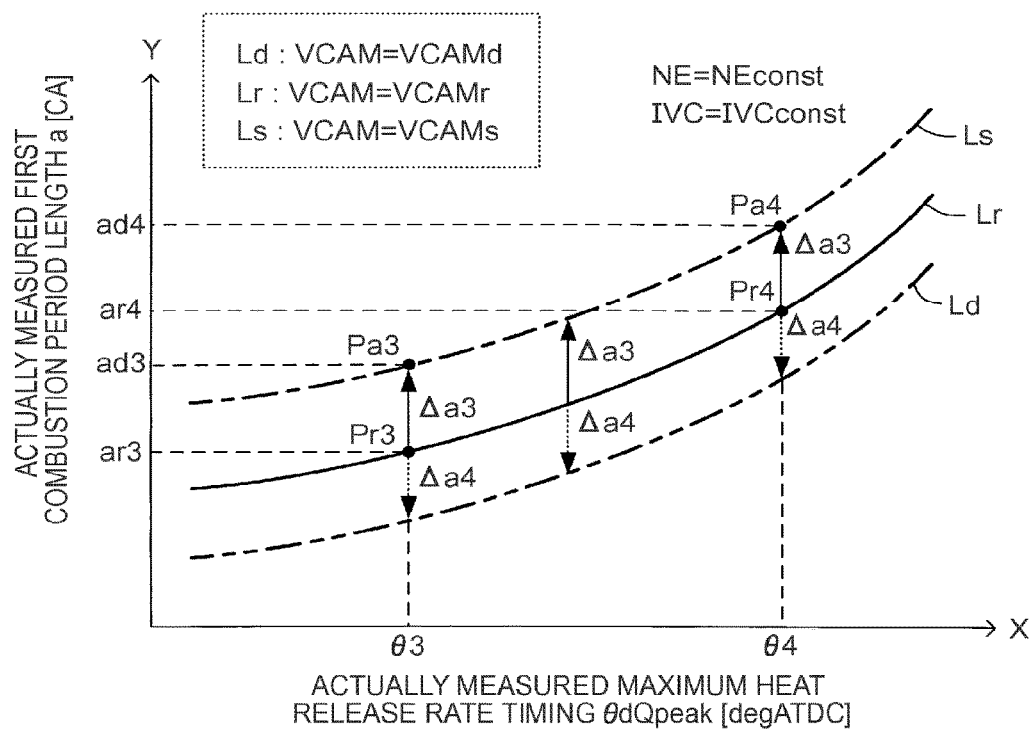
FIG. 3 is a graph that shows the relationship between maximum heat release rate timing and a first combustion period length for each of various intake valve operating angles.
Figure 4A:
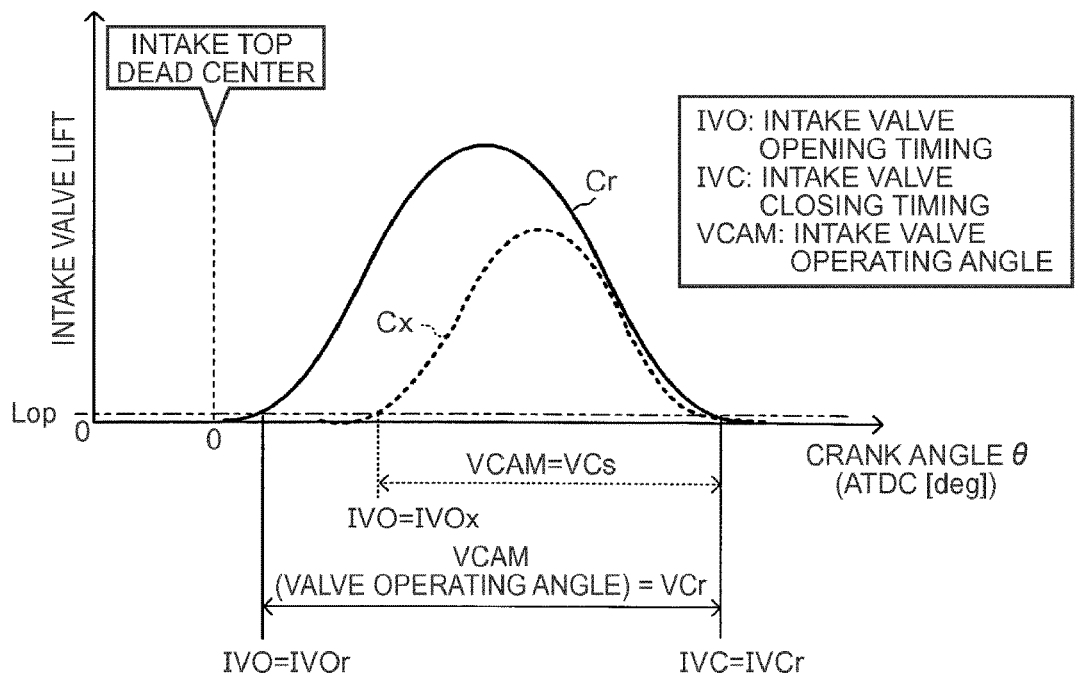
FIG. 4A and FIG. 4B are views for illustrating parameters that define the valve opening characteristic of the intake valve.
Figure 4B:
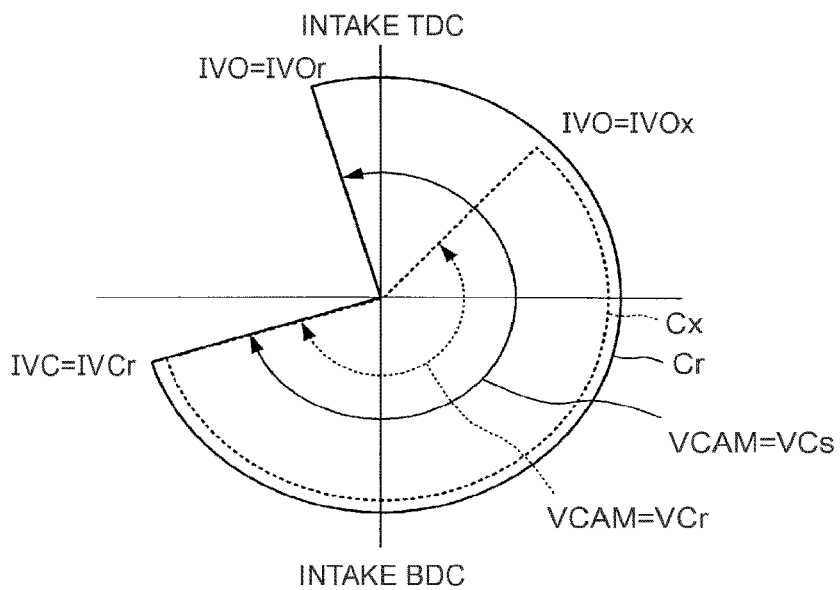

As described with reference to FIG. 3, FIG. 4A and FIG. 4B, the inventor also obtained the following findings 2.

(Findings 2) The relationship (that is, the reference relationship) between the maximum heat release rate timing θdQpeak and the first combustion period length aref in the case where the engine rotation speed NE is the selected speed NE0, the intake valve closing timing IVC is selected valve closing timing IVC0 and the intake valve operating angle VCAM is the reference valve operating angle VCAMr is expressed by the function aref=g (θdQpeak). At this time, when it is assumed that the first combustion period length as(θ3) at the time when the engine rotation speed NE is the selected speed NE0, the intake valve closing timing IVC is the selected valve closing timing IVC0, the intake valve operating angle VCAM is the predetermined operating angle VCAMs and the maximum heat release rate timing θdQpeak is a selected value (selected reference value) θ3 is ad3, the first combustion period length as(θ4) at the time when the engine rotation speed NE is the selected speed NE0, the intake valve closing timing IVC is the selected valve closing timing IVC0, the intake valve operating angle VCAM is the predetermined operating angle VCAMs and the maximum heat release rate timing θdQpeak is a selected value θ4 is allowed to be obtained by the use of the following mathematical expression (2B).

$$as(\theta 4)=g(\theta 4)+\Delta a3=g(\theta 4)+(ad3-ar3)=g(\theta 4)-(ar3-ad3)=g(\theta 4)+\{ad3-g(\theta 3)\} \quad (2B)$$

Figure 32:
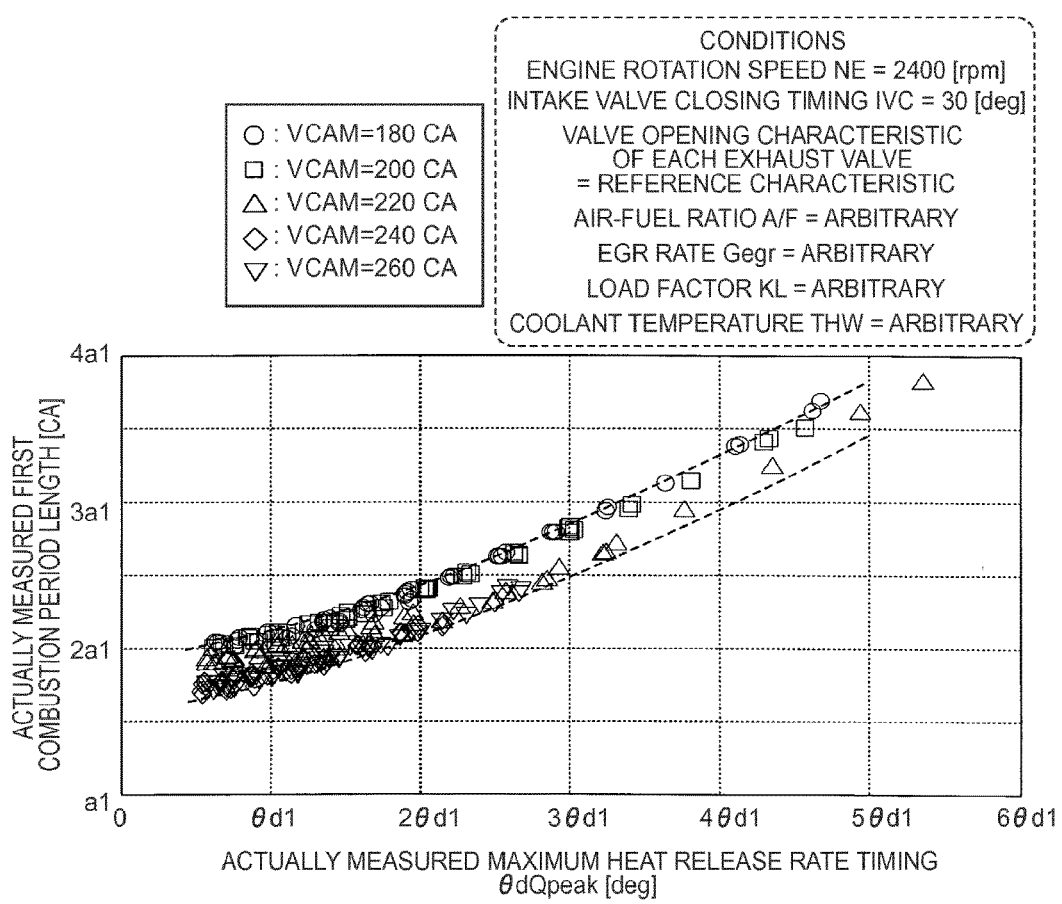
FIG. 32 is a graph that shows the relationship between actually measured maximum heat release rate timings and actually measured first combustion period lengths for each of various intake valve operating angles in the case where the engine rotation speed and the intake valve closing timing are kept constant.

Hereinafter, the validity of the findings 2 will be described. FIG. 32 is a graph in which the relationship between the actually measured maximum heat release rate timings θdQpeak and the actually measured first combustion period lengths a is plotted in experiment in which, when the engine rotation speed NE is a constant speed (=2400 [rpm]), the intake valve closing timing IVC is fixed to predetermined timing (=30[ABDCdeg]) and the intake valve operating angle VCAM is changed to various values.

It is understood from FIG. 32 that curves (dashed lines) that define the relationships between the maximum heat release rate timing θdQpeak and the first combustion period length a strongly correlate with the intake valve operating angle VCAM and are translated in the direction in which the first combustion period length a increases or reduces (in the sheet vertical direction, that is, the Y-axis direction) as the intake valve operating angle VCAM changes.

Figure 33A:
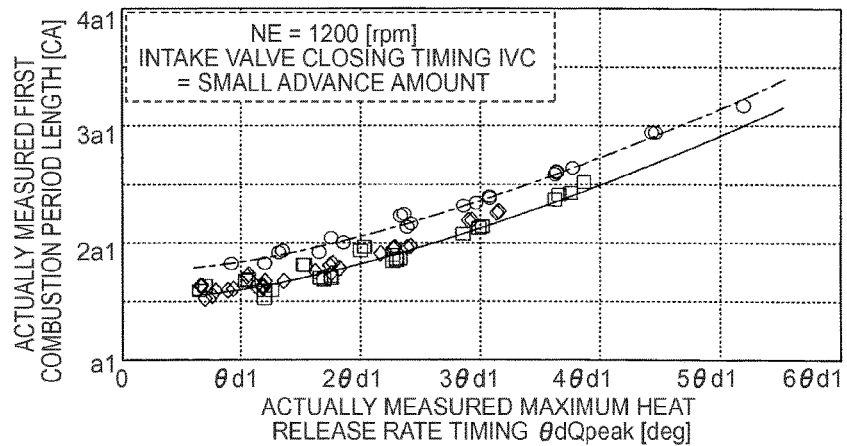
FIG. 33A to FIG. 33C each are a graph that shows the relationship between actually measured maximum heat release rate timings and actually measured first combustion period lengths for each of various intake valve operating angles in the case where the engine rotation speed and the intake valve closing timing are kept constant.
Figure 33B:
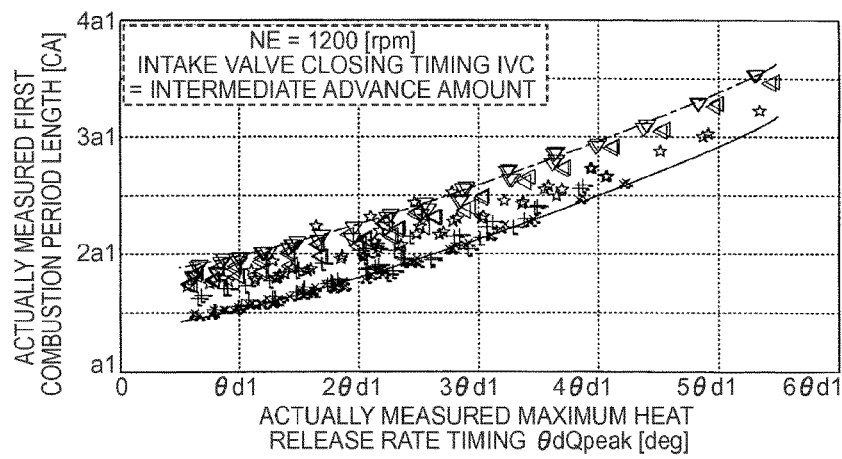
Figure 33C:
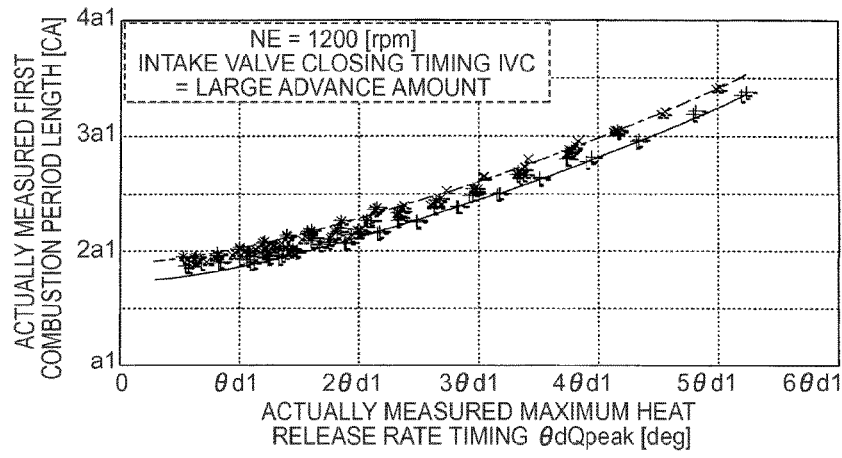

Each of the graphs shown in FIG. 33A to FIG. 33C is a graph in which the relationship between the actually measured maximum heat release rate timings θdQpeak and the actually measured first combustion period lengths a is plotted in experiment in which, when the engine rotation speed NE is 1200 [rpm], the intake valve closing timing IVC is fixed to any one of various values and the intake valve operating angle VCAM is changed to various values.

Legends in the graphs shown in FIG. 33A to FIG. 33C are shown in TABLE 2.

TABLE 2

| ○: VCAM = 110 CA | ▷: VCAM = 210 CA |
|---|---|
| □: VCAM = 140 CA | ☆: VCAM = 220 CA |
| △: VCAM = 160 CA | ✿: VCAM = 230 CA |
| ◇: VCAM = 170 CA | ×: VCAM = 240 CA |
| ▽: VCAM = 180 CA | ✱: VCAM = 250 CA |
| ◁: VCAM = 200 CA | +: VCAM = 260 CA |

The graphs shown in FIG. 33A to FIG. 33C indicate that, when the intake valve closing timing IVC is fixed to any one of various values in the case where the engine rotation speed NE is 1200 [rpm], the relationship is translated in the direction in which the first combustion period length a increases or reduces as the intake valve operating angle VCAM changes.

Figure 34A:
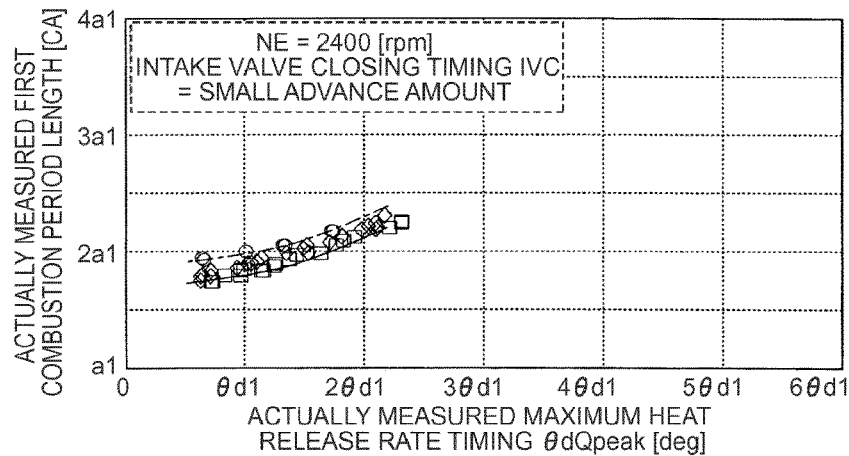
FIG. 34A to FIG. 34C each are a graph that shows the relationship between actually measured maximum heat release rate timings and actually measured first combustion period lengths for each of various intake valve operating angles in the case where the engine rotation speed and the intake valve closing timing are kept constant.
Figure 34B:
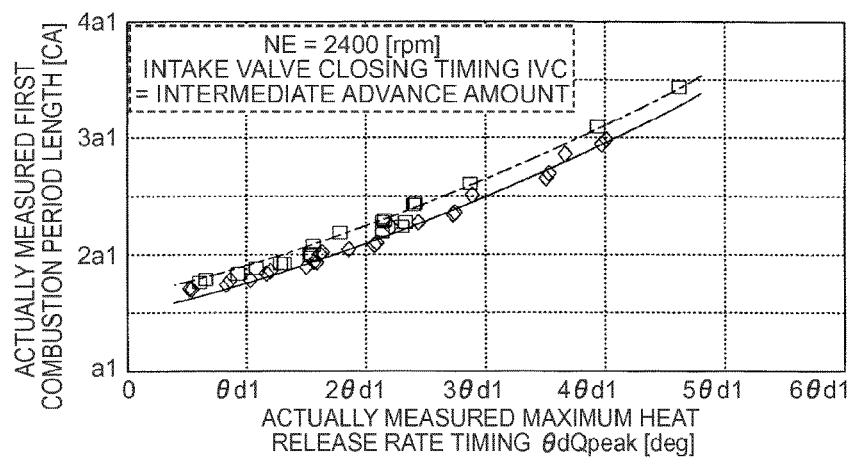
Figure 34C:
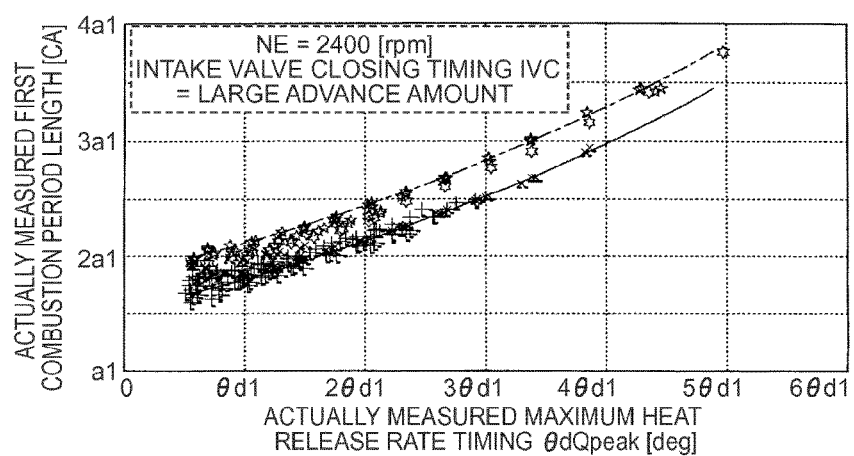

Similarly, each of the graphs shown in FIG. 34A to FIG. 34C is a graph in which the relationship between the actually measured maximum heat release rate timings θdQpeak and the actually measured first combustion period lengths a is plotted in experiment in which, when the engine rotation speed NE is 2400 [rpm], the intake valve closing timing IVC is fixed to any one of various values and the intake valve operating angle VCAM is changed to various values. Legends in the graphs shown in FIG. 34A to FIG. 34C are the same as the legends shown in TABLE 2.

The graphs shown in FIG. 34A to FIG. 34C indicate that, when the intake valve closing timing IVC is fixed to any one of various values in the case where the engine rotation speed NE is 2400 [rpm], the relationship is translated in the direction in which the first combustion period length a increases or reduces as the intake valve operating angle VCAM changes. It is understood from the graphs shown in FIG. 33A to FIG. 33C and the graphs shown in FIG. 34A to FIG. 34C that, even when the engine rotation speed NE is different, as long as the engine rotation speed NE is kept constant and the intake valve closing timing IVC is kept constant, the relationship is translated in the direction in which the first combustion period length a increases or reduces as the intake valve operating angle VCAM changes.

As described above, the validity of the findings 2 is verified by the graphs shown in FIG. 33A to FIG. 33C and FIG. 34A to FIG. 34C. Therefore, the validity of the findings 3 that are derived from the findings 1 and the findings 2 as described above is also verified.

As described above, the embodiment apparatus 10 is able to accurately estimate parameters required to estimate the heat release rate waveform including the first combustion period length a (the ignition delay period length τ, the ignition timing FA, the first combustion period length a, the maximum heat release rate timing θdQpeak, the heat release rate gradient b/a, the heat release amounts Q1, Q2, Qa11, the second combustion period length c, and the like) with the use of the embodiment method. Therefore, it is possible to provide extremely useful information in development, design, and the like, of the internal combustion engine.

Particularly, with the embodiment method, it is possible to easily estimate the first combustion period length a on the basis of the above-described findings 1 and findings 2 even when the valve opening characteristic of each intake valve is a characteristic (specific characteristic) different from a certain reference characteristic. In other words, it is not required to independently create the prediction expression (the above-described mathematical expression (3)) of the first combustion period length a for each valve opening characteristic of each intake valve.

That is, the relationship (reference relationship) between the first combustion period length a and the maximum heat release rate timing θdQpeak in the case where the intake valve opening characteristic is the reference characteristic is acquired with actual measurement or estimation on the basis of the above-described mathematical expression (3), the Wiebe function, or the like, and only one first combustion period length a at certain maximum heat release rate timing θdQpeak in the case where the intake valve opening characteristic is the specific characteristic is acquired (or the first combustion period length a is acquired for two or three mutually different maximum heat release rate timings θdQpeak and then the average of those first combustion period lengths a is obtained). Thus, it is possible to simply estimate the first combustion period length a at any maximum heat release rate timing in different specific characteristics by the use of the above-described mathematical expression (1B) and the above-described mathematical expression (2B).

More specifically, in the embodiment method, the above-described mathematical expression (3) may be employed as the above-described function f(θdQpeak) or function g(θdQpeak).

As described above, the above-described mathematical expression (3) holds irrespective of the load factor KL, the EGR rate Gegr, the air-fuel ratio A/F or the coolant temperature THW (engine warm-up state), so it is not required to independently determine the mathematical expression (C3, α and β that are used in the mathematical expression (3)) by repeatedly carrying out experiment for each of these operating state parameters. Therefore, it is possible to reduce time and effort that are required to obtain the first combustion period length a for a combination of these operating state parameters. Although the same applies to the other model expressions, values that are used in each model expression, such as C3, α and β, are allowed to be determined on the basis of a typical data point.

When the above-described mathematical expression (3) is created, it is possible to estimate the first combustion period length a for selected maximum heat release rate timing θdQpeak in the case where the intake valve opening characteristic is the specific characteristic only by actually measuring only the first combustion period length a at the time when the maximum heat release rate timing θdQpeak is a selected reference value (the above-described θ1 or θ3) in the case where the intake valve opening characteristic is the specific characteristic different from the reference characteristic. As a result, it is possible to significantly reduce time and effort that are required to obtain the first combustion period length a.

FIRST APPLICATION EXAMPLE

Figure 35:
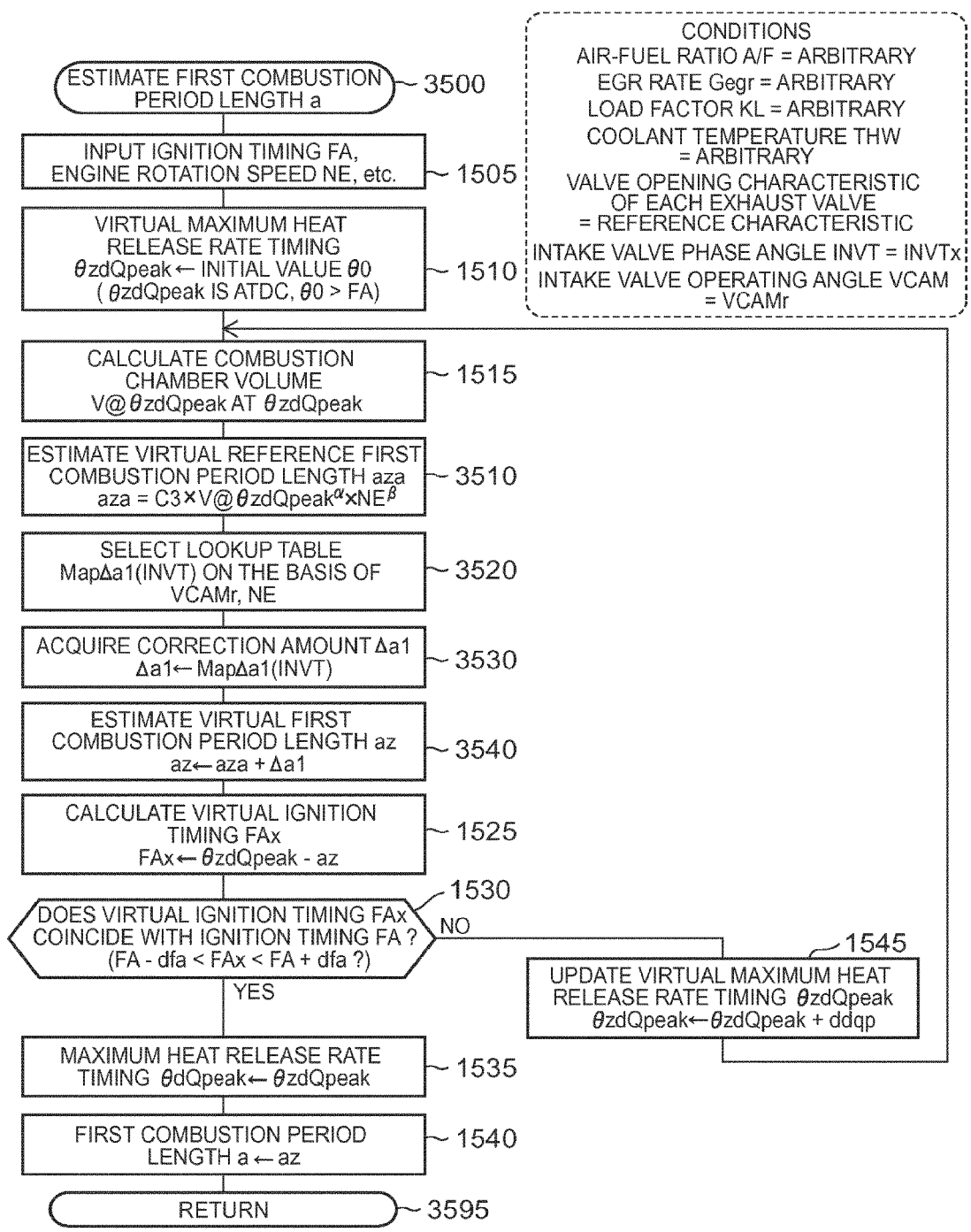
FIG. 35 is a routine that shows an example of application of the embodiment method.

For example, the above-described mathematical expression (3) and the findings 1 (the above-described mathematical expression (1A) or mathematical expression (1B)) of the embodiment method are also used in the routine shown by the flowchart in FIG. 35. This routine is used instead of the routine shown in FIG. 15 when the intake valve phase angle INVT is a specific phase angle INVTx and the intake valve operating angle VCAM is the reference valve operating angle VCAMr (that is, when the valve opening characteristic of each intake valve is a specific characteristic that differs from the reference characteristic in only the intake valve phase angle INVT). Hereinafter, this routine will be simply described. Like step numbers denote the steps shown in FIG. 35 and also shown in FIG. 15, and the description of those steps is omitted. The CPU receives the specific phase angle INVTx in step 1505.

When the CPU calculates the combustion chamber volume V@θzdQpeak at the virtual maximum heat release rate timing θzdQpeak in step 1515, the CPU sequentially executes the processes of step 3510 to step 3540, which will be described below, and then proceeds to step 1525.

In step 3510, the CPU calculates a virtual reference first combustion period length aza [CA] by substituting the combustion chamber volume V@θzdQpeak and the engine rotation speed NE into the same mathematical expression as the mathematical expression (3). The virtual reference first combustion period length aza is a reference value of the first combustion period length that is obtained by the use of the above-described mathematical expression (3) created in the case where the intake valve opening characteristic is set to the reference characteristic.

In step 3520, the CPU selects a lookup table MapΔa1 (INVT) on the basis of the reference valve operating angle VCAMr and the engine rotation speed NE. The table MapΔa1(INVT) is stored in a memory for each combination of the reference valve operating angle VCAMr and the engine rotation speed NE.

The table MapΔa1(INVT) is created in advance on the basis of the above-described findings 1. That is, the table MapΔa1(INVT) is a table in which the amount of increase (which is a value corresponding to (ad1−ar1) in the above-described mathematical expression (1 A), and includes a negative value) Δa1 in first combustion period length a at the time when the maximum heat release rate timing θdQpeak is a selected reference value θ1 for the case where the intake valve phase angle INVT is changed from the reference phase angle INVTr to the predetermined phase angle INVTx in a state where the intake valve operating angle VCAM is kept at the reference valve operating angle VCAMr at the engine rotation speed NE is obtained with actual measurement, calculation, or the like, in advance, and the relationship between the amount of increase Δa1 and the predetermined phase angle INVTx is stored in association with a combination of the reference valve operating angle VCAMr and the engine rotation speed NE.

In step 3530, the CPU acquires the correction amount Δa1 by applying the intake valve phase angle INVTx to the selected table MapΔa1(INVT) (that is, by using the intake valve phase angle INVTx as a variable (argument) INVT.

In step 3540, the CPU estimates the virtual first combustion period length az by adding the acquired correction amount Δa1 to the virtual reference first combustion period length aza.

In this way, with the embodiment method based on the findings 1, even when the intake valve phase angle INVT changes, it is possible to easily estimate the virtual first combustion period length az. In addition, it is possible to create the table MapΔa1(INVT) with extremely small time and effort in comparison with the case where the above-described mathematical expression (3) is independently created when the intake valve phase angle INVT changes to various values.

SECOND APPLICATION EXAMPLE

Figure 36:
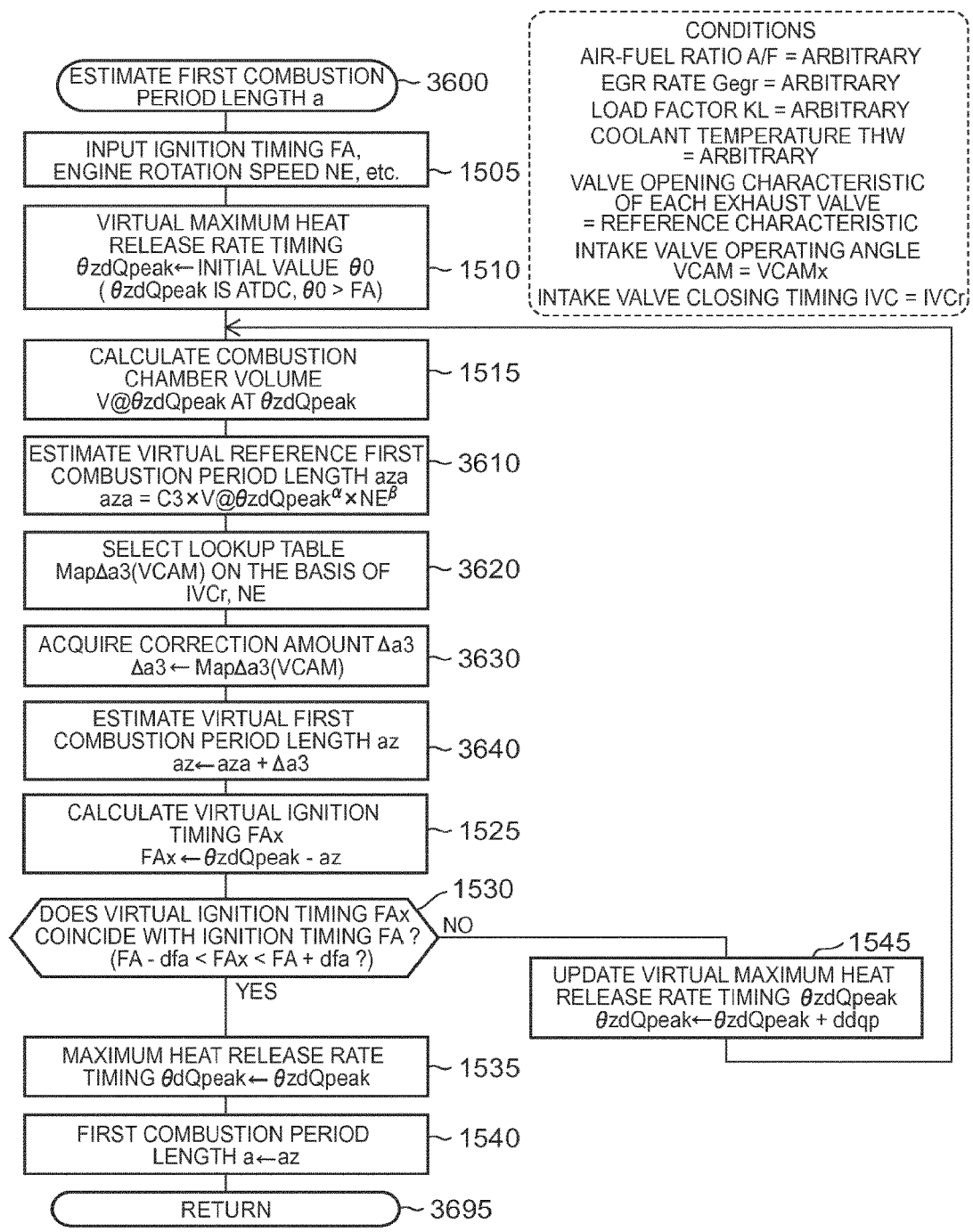
FIG. 36 is a routine that shows an example of application of the embodiment method.

For example, the above-described mathematical expression (3) and the findings 2 (the above-described mathematical expression (2A) or mathematical expression (2B)) of the embodiment method are also used in the routine shown by the flowchart in FIG. 36. This routine is used instead of the routine shown in FIG. 15 when the intake valve operating angle VCAM is the specific operating angle VCAMx and the intake valve closing timing IVC is the reference valve closing timing IVCr (that is, when the valve opening characteristic of each intake valve is a specific characteristic that differs from the reference characteristic in only the intake valve operating angle VCAM). Hereinafter, this routine will be simply described. Like step numbers denote the steps shown in FIG. 36 and also shown in FIG. 15, and the description of those steps is omitted. The CPU receives the specific valve operating angle VCAMx in step 1505.

When the CPU calculates the combustion chamber volume V@θzdQpeak at the virtual maximum heat release rate timing θzdQpeak in step 1515, the CPU sequentially executes the processes of step 3610 to step 3640, and then proceeds to step 1525.

In step 3610, the CPU calculates the virtual reference first combustion period length aza [CA] by substituting the combustion chamber volume V@θzdQpeak and the engine rotation speed NE into the same mathematical expression as the above-described mathematical expression (3). The virtual reference first combustion period length aza is a reference value of the first combustion period length, which is obtained by the use of the above-described mathematical expression (3) created for the case where the intake valve opening characteristic is set to the reference characteristic (the case where the intake valve phase angle INVT is set to the reference phase angle INVTr and the intake valve operating angle VCAM is set to the reference valve operating angle VCAMr).

In step 3620, the CPU selects a lookup table MapΔa3 (VCAM) on the basis of a combination of the reference valve closing timing IVCr and the engine rotation speed NE. The table MapΔa3(VCAM) is stored in the memory for each combination of the reference valve closing timing IVCr and the engine rotation speed NE.

The table MapΔa3(VCAM) is created in advance on the basis of the above-described findings 2. That is, the table MapΔa3(VCAM) is a table in which the amount of increase (which is a value corresponding to (ad3−ar3) in the above-described mathematical expression (2A), and includes a negative value) Δa3 in first combustion period length a at the time when the maximum heat release rate timing θdQpeak is a selected reference value θ3 for the case where the intake valve operating angle VCAM is changed from the reference valve operating angle VCAMr to the predetermined operating angle VCAMx in a state where the intake valve closing timing IVC is kept at the reference valve closing timing IVCr at the engine rotation speed NE is obtained with actual measurement, calculation, or the like, in advance, and the relationship between the amount of increase Δa3 and the predetermined operating angle VCAMx is stored in association with a combination of the reference valve closing timing IVCr and the engine rotation speed NE.

In step 3630, the CPU acquires the correction amount Δa3 by applying the operating angle VCAMx to the selected table MapΔa3(VCAM) (that is, by using the valve operating angle VCAMx as a variable (argument) VCAM).

In step 3640, the CPU estimates the virtual first combustion period length az by adding the acquired correction amount Δa3 to the virtual reference first combustion period length aza.

In this way, with the embodiment method based on the findings 2, even when the intake valve operating angle VCAM changes, it is possible to easily estimate the virtual first combustion period length az. In addition, it is possible to create the table MapΔa3(VCAM) with extremely small time and effort in comparison with the case where the above-described mathematical expression (3) is independently created when the intake valve operating angle VCAM changes to various values.

As described above, with the embodiment apparatus 10 and the embodiment method, the first combustion period length a that is one of important parameters indicating a combustion state is accurately estimated in response to the valve opening characteristic of each intake valve with less effort. Therefore, it is possible to reduce man-hours for development of an internal combustion engine. Even if the other parameters that indicate a combustion state (such as the ignition delay period length τ and the heat release rate gradient b/a) differ from true values due to the influence of the intake valve opening characteristic, at least the first combustion period length a accurately reflects the intake valve opening characteristic, so it is also possible to improve the accuracy of the heat release rate waveform as a whole.

The invention is not limited to the above-described embodiment. Various alternative embodiments may be employed within the scope of the invention. For example, the above-described findings 1 and findings 2 may be used in combination. That is, the relationship between the maximum heat release rate timing θdQpeak and the first combustion period length a in the case where the intake valve phase angle INVT is the reference phase angle INVTr and the intake valve operating angle VCAM is the reference valve operating angle VCAMr is obtained in advance as a reference function f1, and a function f2 that expresses the relationship between the maximum heat release rate timing θdQpeak and the first combustion period length a in the case where only the intake valve phase angle INVT is changed to the phase angle INVTx is initially obtained on the basis of the above-described findings 1. The function f2 is set as a new reference function (that is, the phase angle INVTx is regarded as the reference phase angle), and a function f3 that expresses the relationship between the maximum heat release rate timing θdQpeak and the first combustion period length a in the case where only the intake valve operating angle VCAM is changed to the operating angle VCAMx is obtained on the basis of the above-described findings 2.

Alternatively, the first combustion period length a (virtual first combustion period length az) at the time when the intake valve phase angle INVT and the intake valve operating angle VCAM have changed from those of the reference characteristic (that is, the reference phase angle INVTr and the reference valve operating angle VCAMr) may be estimated in the following manner. A correction amount Aa that is added to the virtual reference first combustion period length aza in step 3540 or step 3640 is obtained as a table MapΔa(NE, INVT, VCAM), the correction amount Δa is acquired by applying an actual engine rotation speed NE, intake valve phase angle INVTx and intake valve operating angle VCAMx to the table MapΔa(NE, INVT, VCAM), and then the correction amount Δa (Δa1 or Δa3) is added to the virtual reference first combustion period length aza.

The table MapΔa(NE, INVT, VCAM) is created in advance on the basis of the above-described findings 1 and findings 2. That is, the table MapΔa(NE, INVT, VCAM) is a table in which the amount of increase (correction amount, differential value) Δa in first combustion period length a at the time when the maximum heat release rate timing θdQpeak is a selected reference value θ1 in the case where the intake valve phase angle INVT has been changed to a selected phase angle INVTx and the intake valve operating angle VCAM has been changed to a selected valve operating angle VCAMx at the engine rotation speed NE in a state where the intake valve phase angle INVT is set to the reference phase angle INVTr and the intake valve operating angle VCAM is set to the reference valve operating angle VCAMr at the engine rotation speed NE is obtained with actual measurement, calculation, or the like, in advance, and the amount of increase Aa is stored in association with the engine rotation speed NE, the selected phase angle INVTx and the selected valve operating angle VCAMx.

Therefore, the step of obtaining the correction amount (differential value) Δa (step corresponding to step 3530 or step 3630) corresponds to executing a step (first step) of acquiring a first combustion period length at the time when maximum heat release rate timing is predetermined first timing (selected reference value θ1) in a reference state as a first reference period length on the basis of a reference relationship (reference function f1), the reference state being a state where an engine rotation speed is a predetermined reference rotation speed and a valve opening characteristic of each intake valve of an engine is set to a predetermined reference valve opening characteristic; a step (second step) of acquiring the first combustion period length at the time when the maximum heat release rate timing is the first timing in a specific state as a first specific period length with actual measurement, the specific state being a state where the engine rotation speed is the reference rotation speed and the valve opening characteristic of each intake valve is set to a specific valve opening characteristic different from the reference valve opening characteristic; and a step (third step) of acquiring a first differential value (for example, Δa1=ad1−ar1 or Δa3=ad3−ar3) by subtracting the first reference period length from the first specific period length or acquiring a second differential value (for example, −Δa1=ar1 −ad1 or −Δa3=ar3−ad3) by subtracting the first specific period length from the first reference period length. In the first step, the first reference period length may be obtained with actual measurement.

The step of obtaining the virtual reference first combustion period length aza (step corresponding to step 3510 or step 3610) corresponds to a step (fourth step) of acquiring a first combustion period length at the time when the maximum heat release rate timing is second timing (virtual maximum heat release rate timing θzdQpeak) different from the first timing in the reference state as a second reference period length on the basis of the reference relationship. The step of adding a correction amount Δa (Δa1 or Δa3) to the virtual reference first combustion period length aza (step corresponding to step 3540 or step 3640) corresponds to a step (fifth step) of estimating a first combustion period length (virtual first combustion period length az) at the time when the maximum heat release rate timing is the second timing in the specific state by adding the first differential value (Δa1, Δa3) to the second reference period length (virtual reference first combustion period length aza) or by subtracting the second differential value (−Δa1 , −Δa3) from the second reference period length (virtual reference first combustion period length aza).

When any one of the preconditions for the model expressions do not hold, a correction coefficient for the condition that does not hold may be obtained separately, and each of the ignition delay period length τ, the first combustion period length a and the heat release rate gradient b/a may be corrected by using the correction coefficient.

What is claimed is:
1. A combustion state estimation method comprising:
   acquiring a relationship between a first combustion period length and maximum heat release rate timing in a reference state as a reference relationship with estimation or actual measurement, the reference state being a state where a rotation speed of a spark-ignition internal combustion engine is a predetermined reference rota- tion speed and a valve opening characteristic of an intake valve of the engine is set to a predetermined reference valve opening characteristic, the first combustion period length being a duration of a first combustion period, the first combustion period being a period from ignition timing of fuel in a combustion chamber of the engine to the maximum heat release rate timing, the maximum heat release rate timing being timing at which a rate of release of heat resulting from combustion of the fuel is maximum;

estimating a relationship between the maximum heat release rate timing and the first combustion period length in a specific state on the basis of the reference relationship, the specific state being a state where the rotation speed of the engine is the reference rotation speed and the valve opening characteristic of the intake valve is set to a specific valve opening characteristic different from the reference valve opening characteristic;

acquiring the first combustion period length at the time when the maximum heat release rate timing is predetermined first timing in the reference state as a first reference period length on the basis of the reference relationship or with actual measurement;

acquiring the first combustion period length at the time when the maximum heat release rate timing is the first timing in the specific state as a first specific period length with actual measurement;

acquiring a first differential value by subtracting the first reference period length from the first specific period length or acquiring a second differential value by subtracting the first specific period length from the first reference period length;

acquiring the first combustion period length at the time when the maximum heat release rate timing is second timing different from the first timing in the reference state as a second reference period length on the basis of the reference relationship; and estimating the first combustion period length at the time when the maximum heat release rate timing is the second timing in the specific state by adding the first differential value to the second reference period length or subtracting the second differential value from the second reference period length.

2. The combustion state estimation method according to claim 1, wherein
the specific valve opening characteristic differs from the reference valve opening characteristic in at least one of valve closing timing of the intake valve and an intake valve operating angle that a period during which the intake valve is open is expressed by a crank angle width.

3. The combustion state estimation method according to claim 2, wherein
the reference valve opening characteristic is such a characteristic that the intake valve operating angle is a predetermined reference valve operating angle and an intake valve phase angle is a predetermined reference phase angle, the intake valve phase angle is a crank angle difference between a predetermined reference crank angle and a crank angle that indicates a center between valve opening timing of the intake valve and the valve closing timing of the intake valve, and
the specific valve opening characteristic is such a characteristic that the valve closing timing of the intake valve is different from the valve closing timing of the intake valve in the reference valve opening characteristic because the intake valve operating angle is the reference valve operating angle and the intake valve phase angle is a specific phase angle different from the reference phase angle.

4. The combustion state estimation method according to claim 2, wherein
the reference valve opening characteristic is such a characteristic that the valve closing timing of the intake valve is predetermined reference valve closing timing and the intake valve operating angle is a predetermined reference valve operating angle, and
the specific valve opening characteristic is such a characteristic that the valve closing timing of the intake valve is the reference valve closing timing and the intake valve operating angle is a specific valve operating angle different from the reference valve operating angle.

* * * * *